United States Patent
Sehat

(10) Patent No.: US 10,959,717 B2
(45) Date of Patent: Mar. 30, 2021

(54) METHOD AND APPARATUS FOR JOINT RECONSTRUCTION

(71) Applicant: IMPLANTCAST GMBH, Buxtehude (GB)

(72) Inventor: Khosrow R. Sehat, Nottingham (GB)

(73) Assignee: IMPLANTCAST GMBH, Buxtehude (GB)

( * ) Notice: Subject to any disclaimer, the term of this patent is extended or adjusted under 35 U.S.C. 154(b) by 481 days.

(21) Appl. No.: 15/523,105

(22) PCT Filed: Nov. 6, 2015

(86) PCT No.: PCT/EP2015/075985
§ 371 (c)(1),
(2) Date: Apr. 28, 2017

(87) PCT Pub. No.: WO2016/071516
PCT Pub. Date: May 12, 2016

(65) Prior Publication Data
US 2017/0333018 A1    Nov. 23, 2017

(30) Foreign Application Priority Data

Nov. 7, 2014 (GB) ..................................... 1419876
Feb. 26, 2015 (GB) ..................................... 1503242

(51) Int. Cl.
*A61B 17/02* (2006.01)
*A61B 17/15* (2006.01)
(Continued)

(52) U.S. Cl.
CPC .......... *A61B 17/025* (2013.01); *A61B 17/157* (2013.01); *A61B 17/1764* (2013.01);
(Continued)

(58) Field of Classification Search
CPC . A61B 17/025; A61B 17/0268; A61B 17/155; A61B 17/157; A61B 17/1764
See application file for complete search history.

(56) References Cited

U.S. PATENT DOCUMENTS

| 4,938,762 A | * | 7/1990 | Wehrli | ............... A61B 17/154 606/88 |
| 6,296,646 B1 | * | 10/2001 | Williamson | ......... A61B 17/154 606/90 |

(Continued)

FOREIGN PATENT DOCUMENTS

WO       2013013094       1/2013

OTHER PUBLICATIONS

Attune™ Knee System Fixed Bearing Knee (2013) DePuy Synthesis; 1-71.

*Primary Examiner* — Matthew J Lawson
(74) *Attorney, Agent, or Firm* — Edward J. Baba; Bozicevic, Field & Francis LLP

(57) ABSTRACT

Apparatus and methods for replacing a knee joint with an implant prosthesis are described. The method includes distracting the knee, locating the pre-diseased joint line of the knee and referencing cuts to the femur and tibia in the coronal plane relative to the joint line. The method further comprises determining the posterior slope of a cut to the tibia in the sagittal plane such that the gaps between the tibia and femur in extension and flexion are substantially equal. Apparatus for use in the method is described, including a distractor for distracting the joint, a joint level finder for finding the pre-diseased joint line and a flexion gap optimisation device.

12 Claims, 24 Drawing Sheets

(51) Int. Cl.
*A61B 17/17* (2006.01)
*A61F 2/46* (2006.01)

(52) U.S. Cl.
CPC .... *A61F 2/4657* (2013.01); *A61B 2017/0268* (2013.01); *A61F 2002/4661* (2013.01)

(56) References Cited

U.S. PATENT DOCUMENTS

| | | | | |
|---|---|---|---|---|
| 7,285,122 | B2 * | 10/2007 | Sanford | A61B 17/154 606/87 |
| 7,569,060 | B2 * | 8/2009 | Faoro | A61B 17/157 606/87 |
| 8,092,462 | B2 * | 1/2012 | Pinczewski | A61B 17/154 606/88 |
| 8,114,083 | B2 * | 2/2012 | Haines | A61B 17/15 606/79 |
| 2005/0149040 | A1 * | 7/2005 | Haines | A61B 17/155 606/88 |
| 2006/0217732 | A1 | 9/2006 | Seo et al. | |
| 2007/0021383 | A1 | 1/2007 | Loder | |
| 2008/0262500 | A1 | 10/2008 | Collazo | |
| 2009/0043310 | A1 | 2/2009 | Rasmussen | |
| 2011/0106092 | A1 | 5/2011 | Fisher et al. | |
| 2012/0245588 | A1 * | 9/2012 | Murray | A61B 17/157 606/87 |
| 2012/0323246 | A1 * | 12/2012 | Catanzarite | A61B 17/157 606/88 |

* cited by examiner

Things to do before using FGOD

Adjust the anterior referencing bar according to femoral size

Adjust the FGOD according to tibial size

Attach FGOD

Attach DFCSB with anterior referencing guide

Pin DFCSB onto distal femur

Attach ruler to measure femur size

Adjust to next bigger implant size an insert final tibial pins

METHOD AND APPARATUS FOR JOINT RECONSTRUCTION

The present disclosure relates to arthroplasty of the knee (primarily) with adaptation for arthroplasty of other joints being possible. It also relates to the instruments and computer navigation workflow for the procedure described.

Knee and other joint arthroplasty surgery are commonly performed operations for advanced degenerative disease of the joint. The operation involves excision of the diseased articular surfaces of the joint and their replacement with prosthetic joint components. The soft tissues of the joint (ligaments, capsule, muscle and tendons) are generally retained in the surgery and necessary for function of the knee after replacement. In knee arthroplasty, the articular surfaces of the femur and tibia are resected and replaced with femoral and tibial prostheses respectively. Joint motion is produced by the articulation of the prostheses articular surfaces. The motion is guided by the native soft tissue. Joint stability and the spatial relationship between the femoral and tibial prostheses components are also largely directed by the soft-tissue.

Joint arthroplasty prostheses generally try to replicate the normal anatomic morphology and surface contours of the pre-diseased joint so as to replicate as closely as possible the motion of the joint being replaced. The native joint may otherwise be known as the original or pre-diseased joint. However, the native joint anatomy will be individual and unique to each patient with an infinite variation in dimensions and contours. Prostheses are manufactured to increments of sizes and ratios of dimensions, limited by practicality and management of inventory. Implant longevity is prioritized. Therefore, most patients will receive a prosthesis that is an approximation (or the nearest match) to their individual anatomy. Custom made implants are available but prohibitive in terms of healthcare economics.

For the replaced joint to function satisfactorily and optimally, the prosthesis should be positioned so that its mechanics and motion are congruent with the biomechanics of the soft tissue of the native joint. The tension of the soft tissue structures should be accommodated by the appropriate positioning of the prostheses and/or soft tissue releases directed by the instrumentation. Current methodology uses instrumentation (either manual, computer navigated or cad/cam individual jigs manufactured from a pre-operative cross sectional scan) to position the prosthesis according to established criteria that apply to the 'average' patient. Thus conventional joint replacement is an approximation of the individual anatomy to the nearest sized available prosthesis, positioned according to the alignment of the average subject which will also be an approximation for each unique individuals anatomy. Thereafter, a period of physiotherapy takes place in order to adapt the patient's soft tissue biomechanics to comply with that of the prosthesis implanted. The latter can be a lengthy, labour-intensive and costly process with some outcomes of the surgery being compromised as a consequence. Conventional joint arthroplasty surgery carries an element of uncertainty of the eventual functional outcome. Patient satisfaction rates for existing knee arthroplasty techniques are around 70-80%. Given that the surgery is only performed for cases of severe degenerative disease and patients who have already lost function, such an outcome is acceptable but there is room for improvement.

The present invention seeks to provide individualised and anatomic alignment and positioning of the prosthesis, in order to closely match the unique soft tissue biomechanics of the individual case with greater accuracy than conventional methodology. This means that the biomechanics of the prostheses are made more congruent with the biomechanics of the patient's soft tissue structures; this can reduce the need for soft tissue adaptation and the length and cost of post-operative rehabilitation, and improve the functional outcome and satisfaction rate of the surgery.

Aspects of the present invention are defined in the appended claims.

One aspect of the invention described is a Total Knee Arthroplasty (TKA) (or Total Knee Replacement—TKR) method of alignment, which may offer significant advantages over any current TKA system in terms of anticipated TKA function, longevity, accuracy and ease of use of the instrumentation. The method may be known as "Individualised Anatomic Arthroplasty" (IAA).

An aspect of the invention provides an apparatus for finding the pre-diseased joint line of a knee, the knee comprising a femur having a lateral condyle and a medial condyle at its distal end, and a tibia having a longitudinal axis, the apparatus comprising:

a first gap guide for inserting between the tibia and the medial condyle of the femur and a second gap guide for inserting between the tibia and the lateral condyle of the femur, wherein the gap guides each comprise a main body having a first surface for contacting the femur and a second surface for contacting the tibia, a centre-point lying half way between the first and second surfaces, and a handle extending from the main body; and a frame comprising a first part having first and second holes for receiving the handles of the first and second gap guides respectively, wherein the original joint level of a patient's knee is taken as the line between the centre-point of the first gap guide and the centre-point of the second gap guide.

The first part of the frame may support the handles of the first and second gap guides such that they are parallel to one another. When supported by the frame the handles of the first and second gap guides need not be at the same height in the coronal plane, in fact it is likely that they will be at different heights. The first part of the frame is adjustable such that first and second holes can be moved closer to one another or further away from one another.

The apparatus may include a mount for attachment to an extramedullary rod for aligning with the axis of the tibia. The first part of the frame may be pivotable relative to the mount and therefore pivotable relative to the extramurally rod. The apparatus may include a gauge for indicating the angle between the pre-diseased joint line and the mount, and therefore between the original joint level and the extramedullary rod.

The first part of the frame may be lockable relative to the mount. The frame may include a second part for supporting a pinning block. The second part of the frame may be pivotable relative to the mount. In this way the angle of the second part, and therefore of any pinning block supported therein, can be adjusted relative to an extramedullary rod to which the apparatus us mounted. The second part of the frame may be attached to the first part of the frame by a pivot joint. The second part of the frame may be attached to the mount by a pivot joint.

The apparatus may include a gauge for indicating the angle of the second part of the frame relative to the pre-diseased joint line. This can allow the angle of the pinning block to be offset from pre-diseased joint line by a desired amount if the pre-diseased joint line is deemed to be too steep. The apparatus may include a gauge for indicating the angle of the second part of the frame relative to the mount, and therefore to the extramedullary rod to which the apparatus is mounted.

The apparatus may include a pinning block supported by the second part of the frame. The pinning block may comprise a pair of holes for guiding pins into the tibia or femur. The pinning block may comprise at least one pair of holes, preferably two or three pairs of holes. The pairs of holes may have different spacings between them so as to provide suitability spaced holes for pinning different sized knees.

The second part of the frame may include two arms, a first arm for supporting a pinning block for locating pins in the tibia and a second arm for supporting a pinning block for locating pins in the femur. The second part of the frame may be pivotable relative to the first part of the frame, or relative to the frame or relative to the mount, about a pivot point between its two arms. The apparatus may include a lock for locking the second part of the frame relative to the first part of the frame. The second part of the frame may be lockable in a position where the angle of a line between the two holes of a pair of holes is the pinning block parallel to the original joint line indicated by the apparatus. The angle may be offset from parallel by a desired number of degrees.

In an embodiment the apparatus may comprise only one joint gap guide holder and only one joint gap guide.

Another aspect of the invention provides a method for determining the position of bony cuts to a tibia and femur of a knee joint during knee arthroplasty the knee joint including soft tissue and having a pre-diseased joint position in which the soft tissue of the joint is balanced, a distal end of the femur including a medial condyle and a lateral condyle and a proximal end of the tibia, the tibia having a longitudinal axis, the method including the steps of:
  distracting the knee joint in extension, guided by the soft tissue of the joint to the pre-diseased position of the joint;
  inserting a first joint gap guide either between the tibia and medial condyle of the femur or between the tibia and lateral condyle of the femur, so as to support the knee, wherein the first gap guide has a first surface for contacting the femur and a second surface for contacting the tibia, and a centre-point half way between said first and second surfaces;
  observing a first joint line passing through the centre point of the first joint gap guide;
  planning cuts to the distal femur based on the observed joint line.

The method may include the step of:
  inserting the first joint gap guide between the tibia and medial condyle of the femur and a second joint gap guide between the tibia and lateral condyle of the femur, so as to support the knee in its pre-diseased position, wherein the first and second guides each have a first surface for contacting the femur and a second surface for contacting the tibia, and a centre-point half way between said first and second surfaces.

The method may include the steps of:
  observing the patients' pre-diseased joint line as the line passing through said centre points of the first and second joint gap guides; and
  planning cuts to the distal femur based on patients' pre-diseased joint line.

The distances between the first and second surfaces of the first and second joint gap guides may be different, or the distances may be equal. The method may include the step of opening the knee to remove osteophytes. The method may include the step of drilling a canal along the central longitudinal axis of the femur. The method may include the step of inserting an intramedullary rod into the canal in the femur. The method may include the step of cutting a notch in the distal end of the femur from the anterior face to the drilled canal, such that a distractor may fit into the notch and contact an intramedullary rod extending from the canal.

The method may include the step of attaching an extramedullary rod to the tibia. The method may include the step of inserting a distractor into the joint so that a second projection contacts distal end of the intramedullary rod recessed in the femur, and a first projection contacts the tibial plateau. The first projection may be screwed to the tibial plateau. The method may include the step of positioning a joint level finder device over the joint gap guides so as to determine the angle of the pre-diseased joint line relative to the axis of the tibia. The method may include the step of using the joint level finder device to align the angle of the pinning blocks for the tibia and/or femur with the angle of pre-diseased joint line. The method may include the step of noting the angle of the pre-diseased joint line, and, if the line is too steep, setting the angle of the pinning blocks for the tibia and/or femur at a reduced angle.

Another aspect of the invention provides a method for determining the position of bony cuts to a tibia and femur of a knee joint during knee arthroplasty the knee joint including soft tissue and having a pre-diseased joint position in which the soft tissue of the joint is balanced, a distal end of the femur including a medial condyle and a lateral condyle and a proximal end of the tibia, the tibia having a longitudinal axis, the method including the steps of:
  distracting the knee joint in extension, guided by the soft tissue of the joint to the pre-diseased position of the joint;
  inserting a first joint gap guide between the tibia and medial condyle of the femur and a second joint gap guide between the tibia and lateral condyle of the femur, so as to support the knee in its pre-diseased position, wherein the first and second guides each have a first surface for contacting the femur and a second surface for contacting the tibia, and a centre-point half way between said first and second surfaces;
  observing the patients' pre-diseased joint line as the line passing through said centre points of the first and second joint gap guides;
  planning cuts to the distal femur based on patients' pre-diseased joint line.

The method for determining the position of bony cuts to a tibia and femur of a knee joint during knee arthroplasty may include a method for determining the angle of a cut to be made to a tibia in the sagittal plane. The method may also include the steps of making a cut to a tibia, the cut having a posterior slope in the sagittal plane.

An aspect of the invention provides an apparatus for determining the angle of a cut to be made to a tibia in the sagittal plane, the apparatus comprising:
  a first chassis having a first pair of channels for receiving pins in a tibia; and
  a second chassis having a second pair of channels for receiving pins to be placed in a tibia;
  wherein the second chassis is pivotable about a pivot point so as to change the angle of the second pair of channels relative to the first pair of channels.

In use pins guided by the second pair of channels provide a guide for a cut to the tibia that has a posterior slope in the sagittal plane. The pivot point may be a physical pivot joint joining the first and second chassis. The pivot point may be a theoretical pivot point which when the apparatus is in use may lie within the tibia. In particular, the pivot point may lie a quarter of the way into the tibia from the anterior face of the tibia.

The apparatus may further comprise a bar having a first end attached to the first chassis and a second end for supporting a distal femoral surface block, wherein in use the bar extends substantially parallel to a longitudinal axis of the tibia. The position of the bar may be adjustable in the direction of the longitudinal axis of the tibia so as to adjust the apparatus to fit femurs of different sizes.

Another aspect of the invention provides a method for determining the posterior slope of a cut to be made to a tibia in the sagittal plane, the method comprising:
  providing an apparatus for determining the angle of a cut to be made to a tibia in the sagittal plane, the apparatus comprising a first chassis having a first pair of channels for receiving pins in a tibia; and a second chassis having a second pair of channels for receiving pins to be placed in a tibia; wherein the second chassis is pivotable about a pivot point so as to change the angle of the second pair of channels relative to the first pair of channels;
  distracting the knee joint in flexion, guided by the soft tissue of the joint to the pre-diseased position of the joint;
  measuring the femur with a template to determine its size;
  positioning the first pair of channels over a pair of pins in a tibia;
  adjusting the second chassis relative to the first chassis such that the channels of the second chassis will direct pins into the tibia at a posterior slope in the sagittal plane.

The pins may provide a guide for a cut to the tibia having a posterior slope which will produce a flexion gap between the tibia and femur which is equal to a measured extension gap. The method may include the step of placing pins through the channels in the second chassis and into the tibia. The method may include the step of removing the pins in the tibia which pass through the channels in the first chassis.

The method may include the step of adjusting the apparatus to a setting indicating the closest prosthesis size available for the measured femur.

An aspect of the invention provides a distractor for separating the tibia and femur of a leg when the leg is extended, the distractor comprising:
  first and second projections for inserting between the tibia and femur when the leg is extended, the first projection for contacting the tibial plateau and the second projection for inserting into a notch cut in the anterior distal femur; and
  a distraction mechanism for forcing the first and second projections away from one another so as to separate the tibia and femur in use.

The first projection of the distractor may be securable to the tibial plateau by a screw. The distraction mechanism may include a rack and pinion mechanism. The distractor may be suitable for separating the tibia and femur bones of a patient's leg when the leg is in flexion. The second projection may be shaped to attach to a projection from a femoral intramedullary rod.

An aspect of the invention provides a distractor kit including a drill comprising an elongate rod for making an intramedullary canal in the femur and a mill at a distal end of the drill for making a recess in the distal end of the femur. The distractor kit may comprise a notch cutter for cutting a notch in the anterior distal femur, from the anterior face of the distal femur to the central longitudinal axis of the femur.

The kit may further comprise an intramedullary rod for insertion into a canal along the central longitudinal axis of the femur, the rod having an end portion for supporting the distractor. In use the end portion of the rod may sit within a recess in the distal end of the femur and the second projection of the distractor may contact the end portion of the intramedullary rod.

An aspect of the invention provides a joint gap guide for inserting between the tibia and either the medial or lateral condyle of the femur, the joint gap guide comprising a main body having a first surface for contacting the femur and a second surface for contacting the tibia and a centre point half way between the first and second surfaces.

The stems may be centred on the body, such that the centre of the stem has a fixed relationship relative to the centre of the JGG. The first surface of the joint gap guide may be concave. The joint gap guide may also comprise a stem or handle extending from the main body. This may assist the surgeon in positioning the guides and/or in assessing the position of the centre point of the joint gap guides and therefore the angle of the line between the centre points of the two JGGs relative to the axis of the tibia. The stems may insert into corresponding holes in a joint level finder device. A number of sizes of JGGs may be provided in a kit for use in knee arthroplasty.

An aspect of the present invention provides a kit for determining the position of bony cuts to a tibia and femur of a knee joint during knee arthroplasty, the kit including at least two of the described pieces of apparatus.

A surgical technique and instruments is provided for individualised and anatomical alignment of joint arthroplasty implants for optimised biomechanics and congruity with soft tissue biomechanics. The individual instruments described may be compatible with each other and hence function as one whole system.

The application relates to the technique, associated instrumentation for manual technique and computer navigation software workflow for computer navigated technique. Primary and revision knee arthroplasty may be performed and the technique and instrumentation adapted for arthroplasty of other joints. In brief, the application relates to:
  a) A surgical technique and workflow for the positioning of the implants according to the individual patient anatomy and soft tissue biomechanics with observance of the mechanical axis but also other biomechanical considerations and anatomical landmarks for implant positioning and optimised soft tissue biomechanics, balance and tension.
  b) Novel intramedullary guide rod assembly, permitting full extension of the knee with the rod in-situ.
  c) Novel instruments for the distraction of the joint in flexion and extension before or after any bony resection is performed and measuring the alignment of the limb.
  d) Determination of the level of the joint articulation by means of referencing the joint gaps.
  e) Alignment to the joint level of both the medial and lateral compartments.
  f) Guiding parallel (gap balanced) extension and flexion bony resections with ability for adjustment for the presence of flexion deformity.
  g) Adjustment of the posterior slope in the sagittal plane of the tibial bony resection for exact flexion gap size with the given femoral component AP size.
  h) A computer navigated software algorithm for the same.

i) Associated ancillary instrumentation and cutting guides compatible with the system main components.

In accordance with a first aspect of the present invention, there is provided a method of replacing a section of bone in a joint (for example a knee joint) in a human or animal body with a prosthesis, comprising the steps of:
(a) determining the position of the interface between the two surfaces of the joint in one position (extension) referenced from the surface of the joint whilst adjusting for wear and with the soft tissue distracted (tensioned) to a physiologically sound tension;
(b) optionally similarly determining the position of the interface between the two surfaces of the joint in another position (flexion);
(c) determining the correct planes for resection of bone in accordance with (a), and optionally also with (b);
(d) removing sections of bone determined from (c) in accordance with the dimensions of the prosthesis being implanted; and
(e) fitting a prosthesis in place of the section of bone removed in step (d).

The advantage of this method is that the prosthesis can be fitted such that its surface matches the original interface between the two surfaces of the joint at critical locations which therefore reproduces the arc of motion that the individual patients anatomy prescribes and is therefore matched to the movement of the patella and soft tissue and hence minimises the need for soft tissue adjustment and physiotherapy.

The step of determining one or more of the arcs described above can be carried out by a computer navigation, for example after two or more points are registered on the surface of each half of the joint (the femoral and tibial surfaces in the case of knee arthroplasty) with the knee in distraction. Accordingly, computer software for controlling the above method steps is also provided.

In an alternative embodiment, the surgeon can estimate the orientation of one or more of the described arcs by means of a manual method. This might involve the following steps (described by way of example with reference to knee arthroplasty):

First, the surgeon removes any excess bone growth (osteophytes and remodeled bone) restoring soft tissue condition and distracts the knee joint using a distractor device until the tension in the soft tissue feels natural and balanced. Secondly this procedure opens up a gap between the femur and the tibia where there has been cartilage wear. Thirdly, the femoral and tibial surfaces are cut parallel to the gap and finally the femoral and tibial implants are fitted in place of the removed sections of bone.

This method may be carried out both in flexion and extension of the joint, in other words the distractor functions in both positions.

In another aspect of the invention, there is comprised a system for carrying out the surgical method described above, comprising the following apparatus:
(a) A joint distractor which can function with the joint in extension and in flexion before any bony cuts have been made in order to reference all of the bony cuts with reference to the soft tissue envelope tension. This is achieved by providing apparatus for attaching the distractor to both the femur and the tibia via right-angled anchoring intramedullary rods and/or external jig that may be positioned either in the femur or the tibia including with the knee in full extension. In a further embodiment the distractor and the tibial external jigs may be combined.

(b) A joint level finder comprising a first joint gap guide for abutting a first compartment of the knee, a second joint gap guide for abutting a second compartment of the knee, and a chassis to which both joint gap guides can be attached, wherein the part of the chassis to which the first joint gap guide is attached is movable about an axis relative to the part of the chassis to which the second joint gap guide is attached, and wherein the chassis has a measurement scale for measuring the relative positions of the two compartments of the knee. A plurality of joint gap guides of different sizes may be provided for different joint gaps. The joint level finder device can also simultaneously connect to the tibial external or intramedullary (internal) guide and align to the tibial axis (the vertical posture of the leg). Thus the relationship between the tibial axis and the differing levels of the joint compartments can be observed.

(c) A flexion gap optimisation device having two chassis that can rotate around each other about a point that corresponds to the anterior section of the proximal tibia (corresponding to the plane of contact between tibia and femur with the knee in extension (straight)). In one embodiment the device is mounted onto the pins already placed in the tibia in extension using the joint level finder. This orientates the device to lie parallel with the planned coronal slope of the tibial resection. The second chassis can be adjusted to mark the position of the definitive tibial resection with reference to the femoral size and prosthesis size selected for a precise fit.

In further aspects of the present invention, each of the devices described above are provided separately.

Embodiments of the present invention are described below, by way of example only, with reference to the accompanying drawings, in which.

Figure 18:
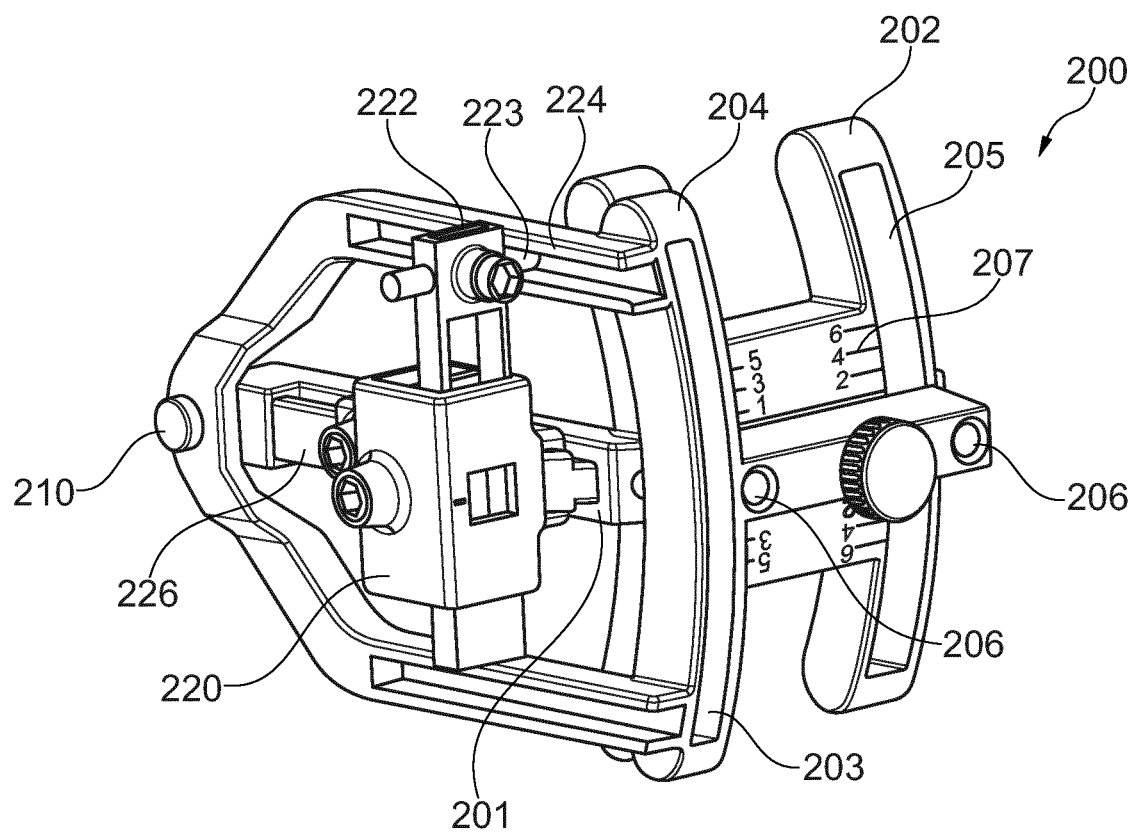
Figure 19:
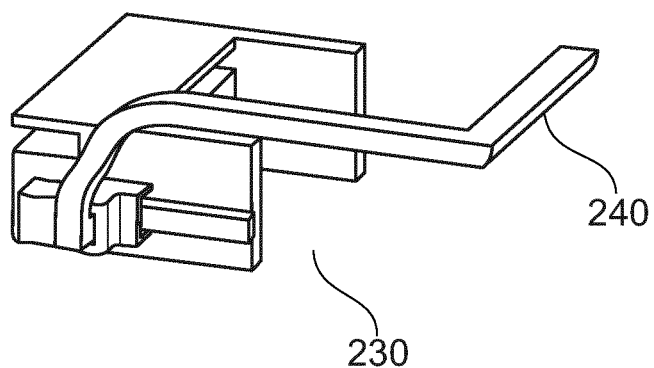
Figure 20:
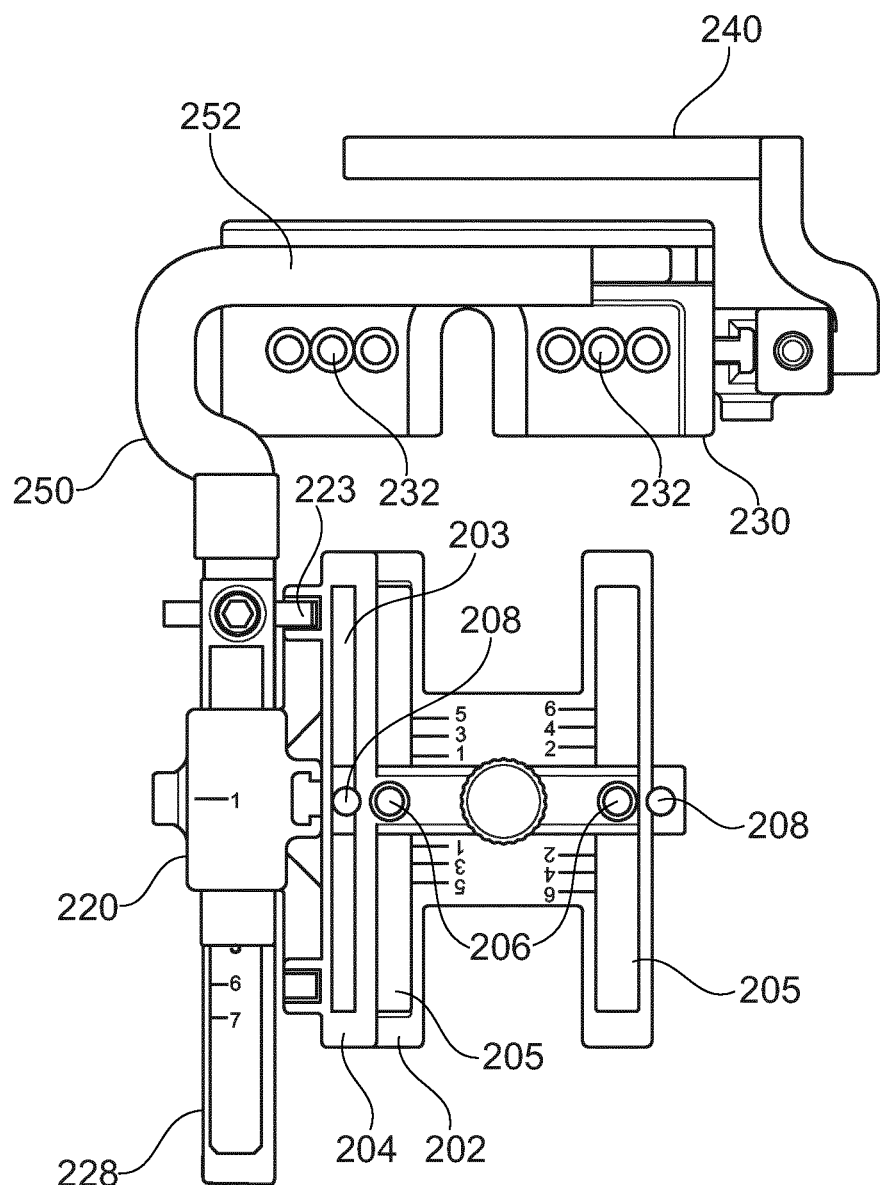
Figure 22:
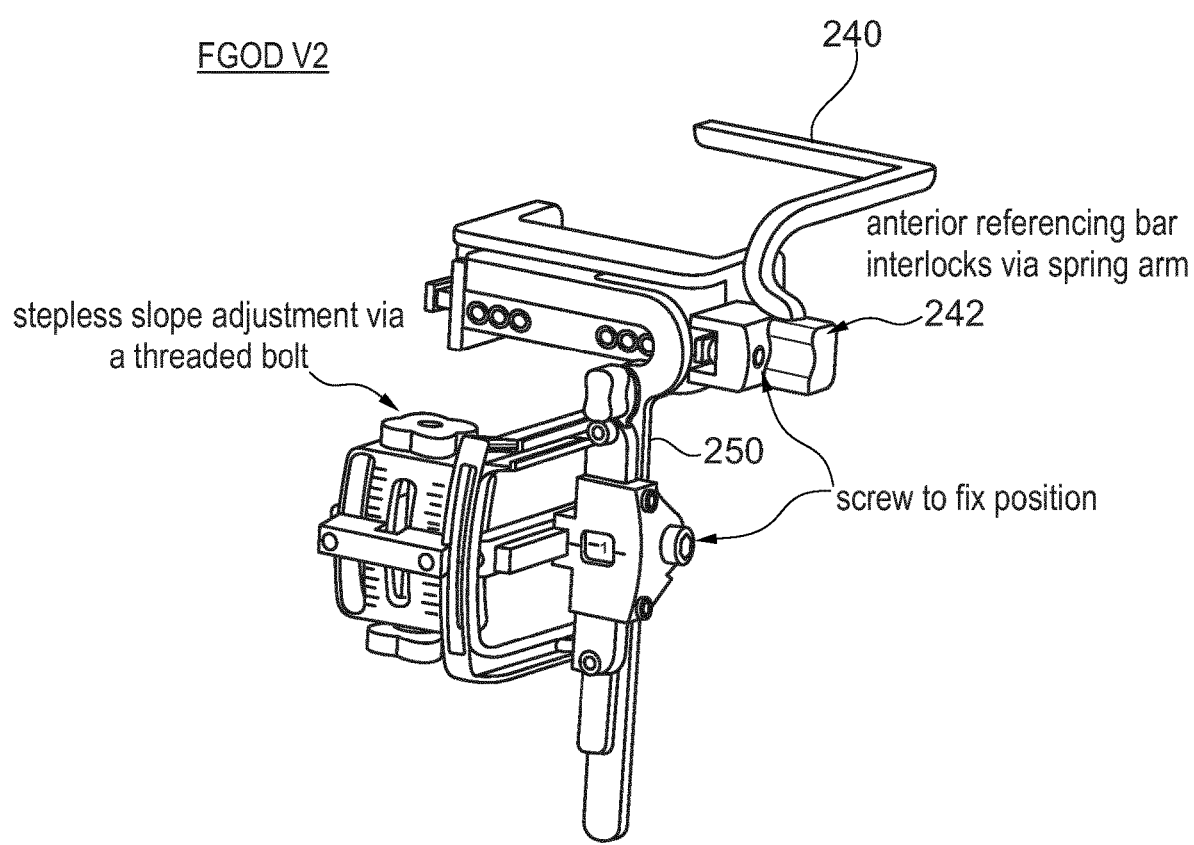
Figure 23A:
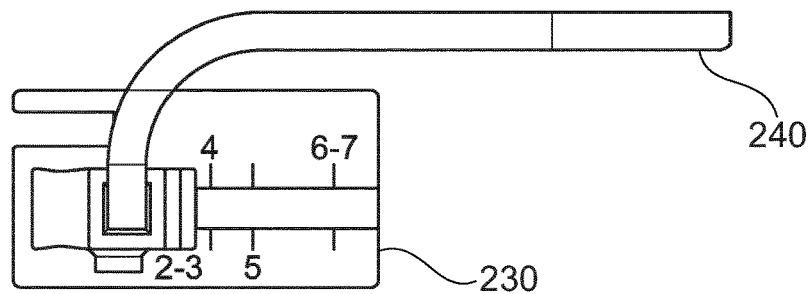
Figure 23B:
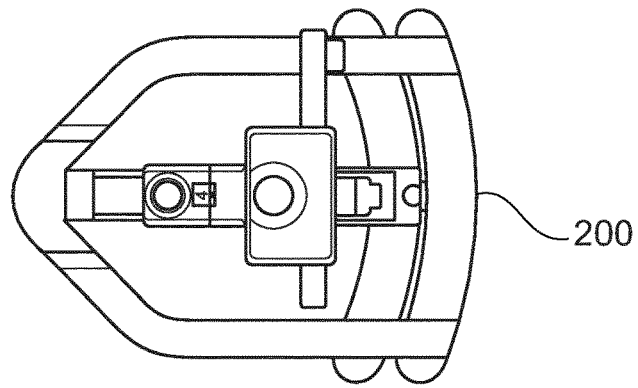
Figure 23C:
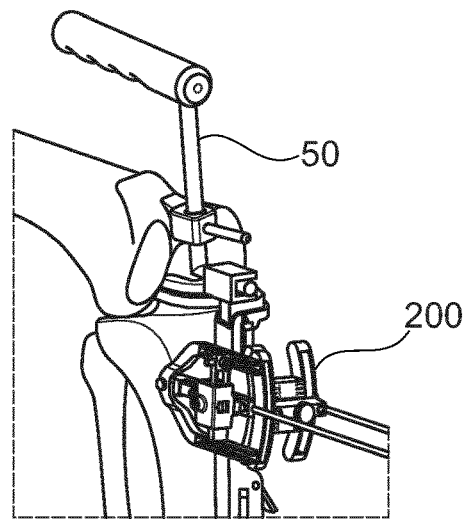
Figure 23D:
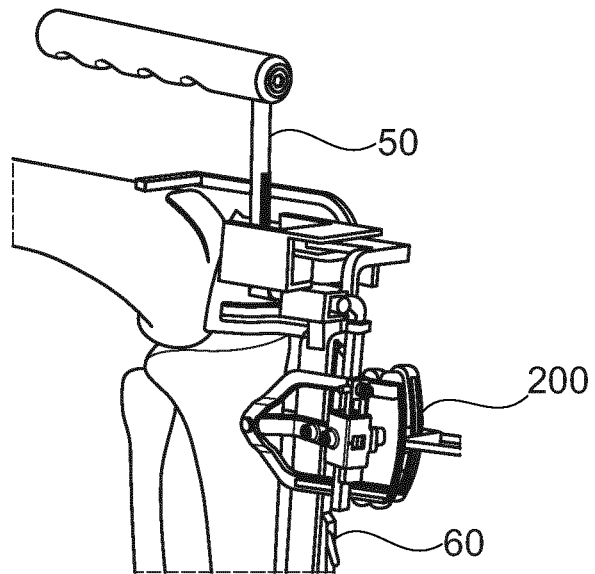
Figure 23E:
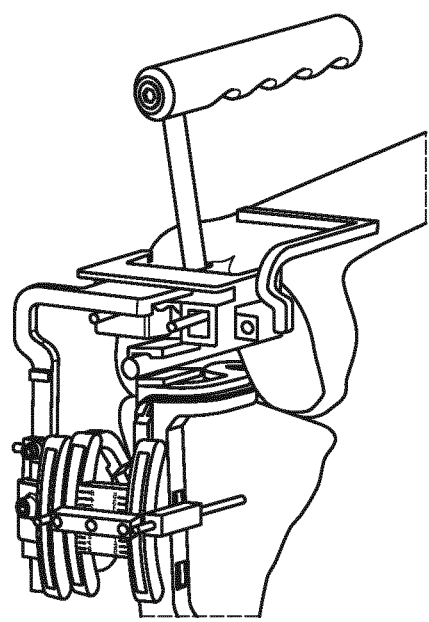
Figure 23F:
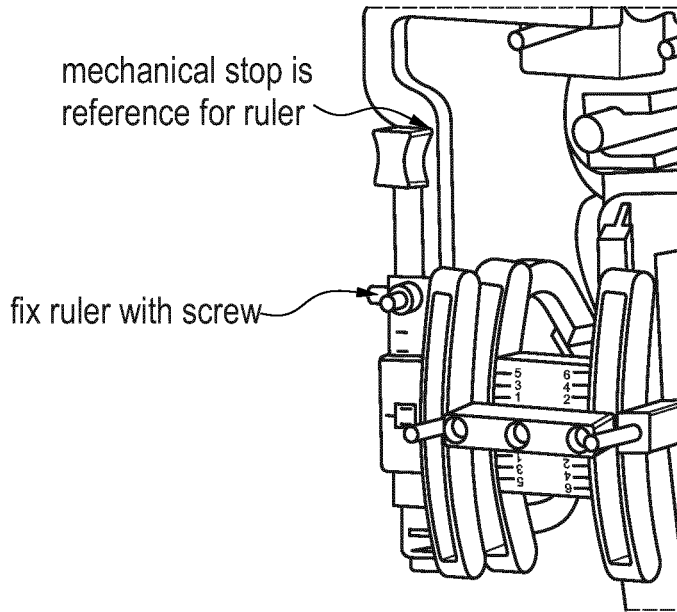
Figure 23G:
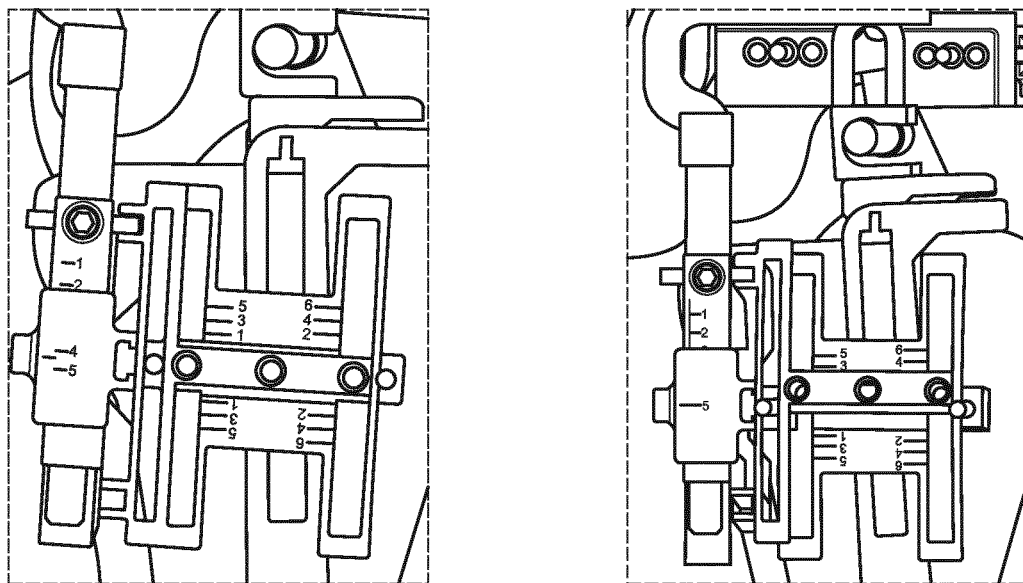
Figure 24A:
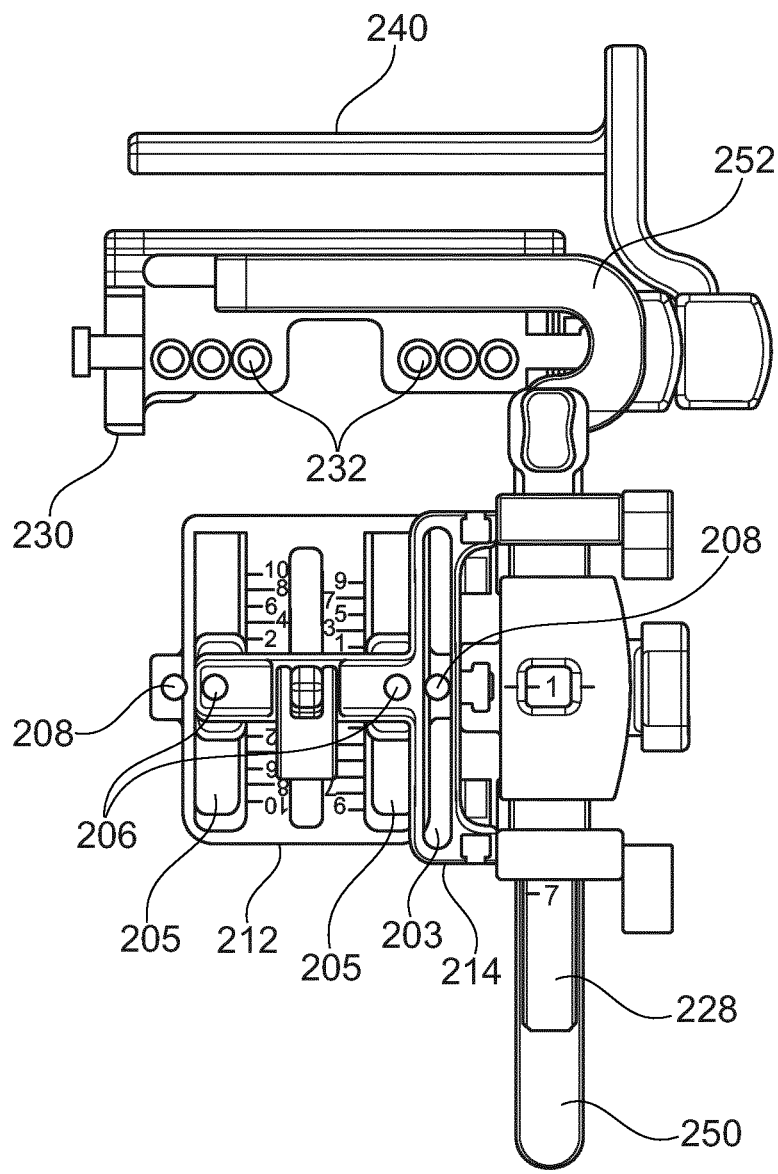
Figure 24B:
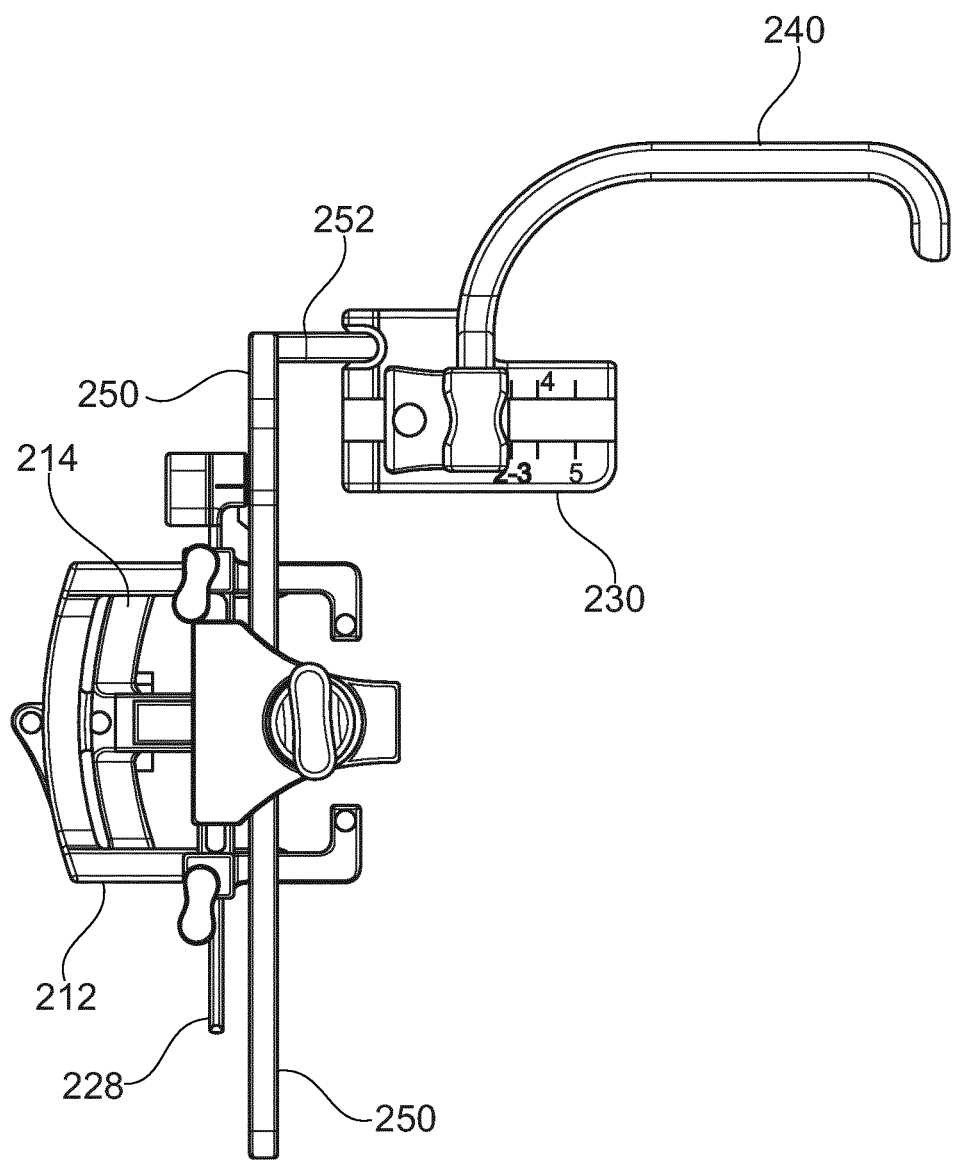
Figure 24C:
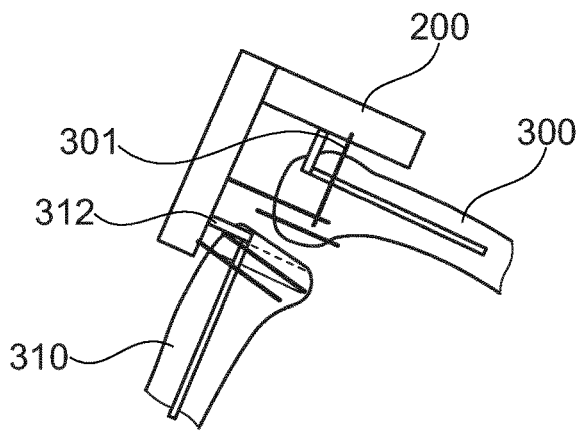
Figure 25:
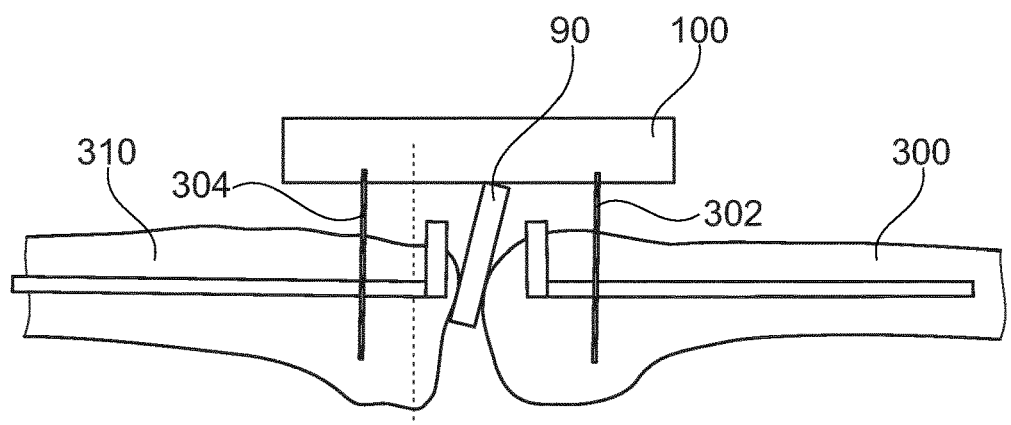
Figure 26:
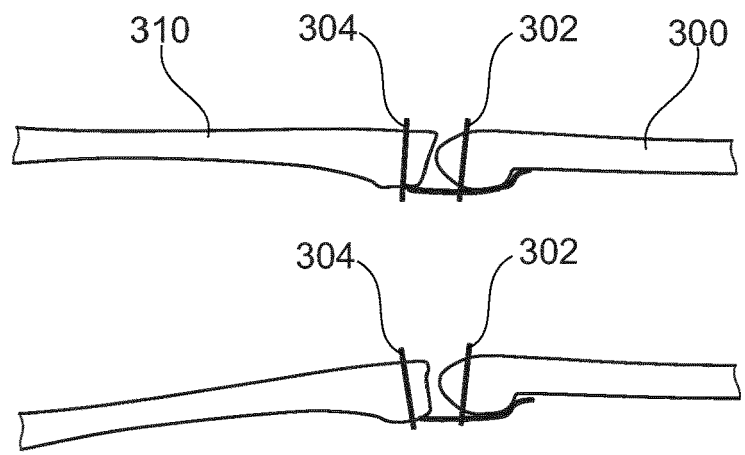
Figure 27:
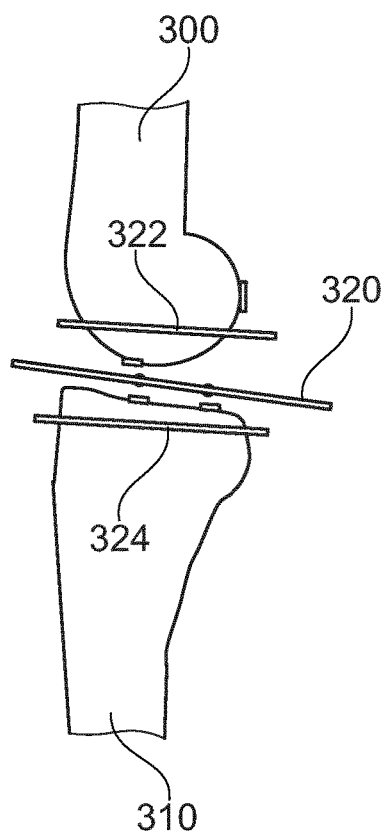
Figure 28:
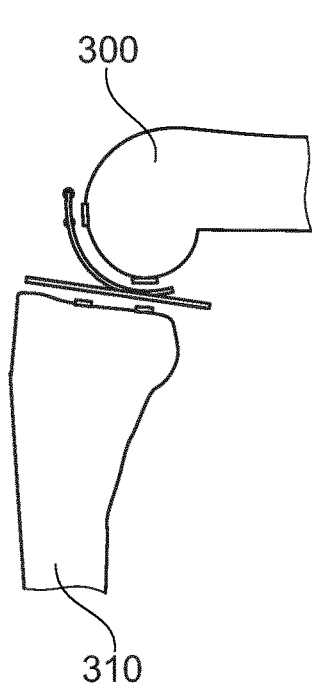
Figure 29:
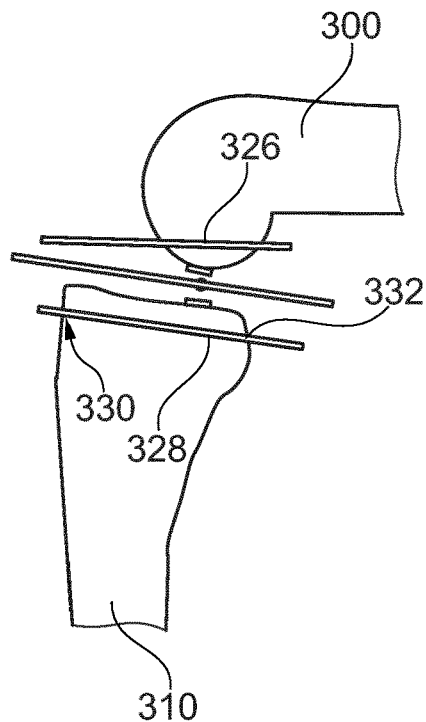
Figure 30:
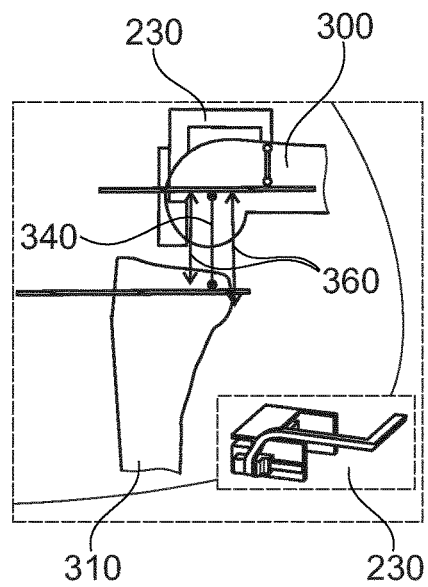
Figure 31:
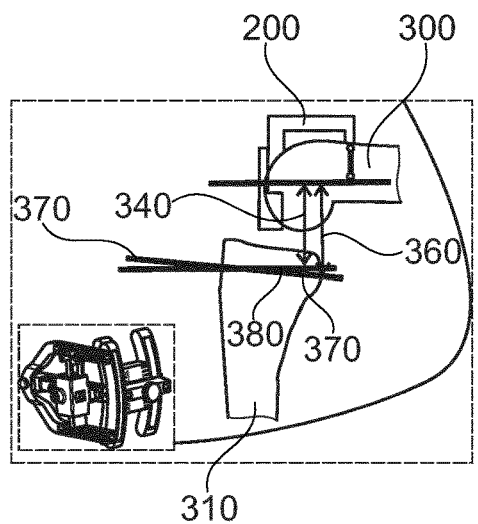
Figure 32:
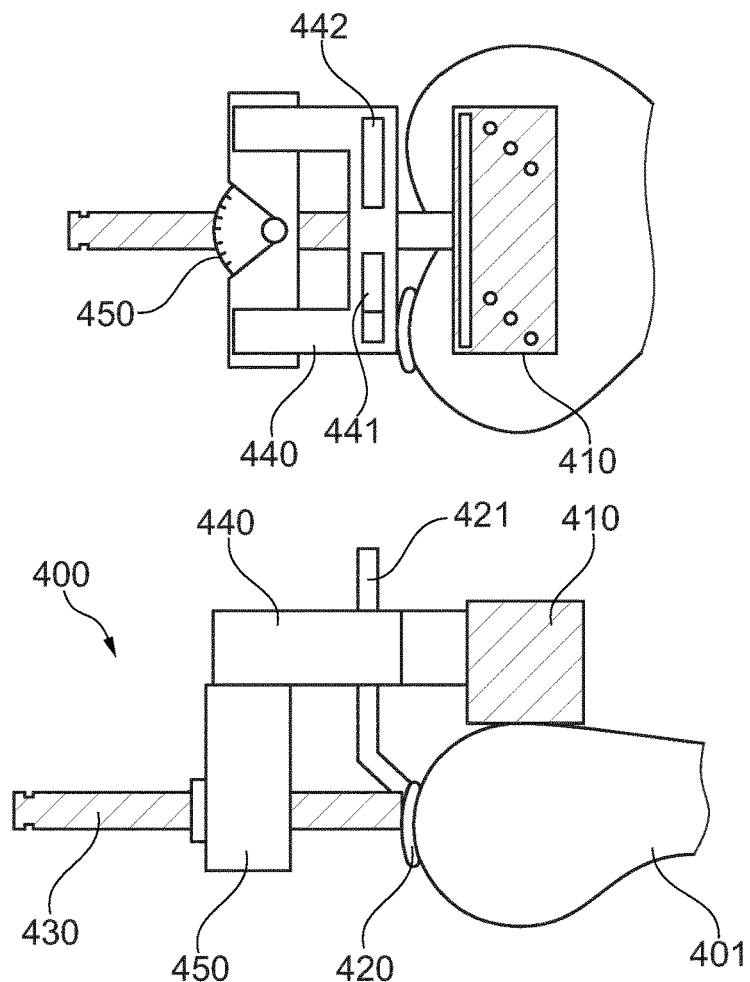

FIG. 17a to f show another Joint Level Finder (JLF), associated pinning blocks, the action of the JLF whereby the pinning blocks can be angulated and the assembly mounted onto the tibial extramedullary guide and distractor together with joint gap guides in-situ and pins placed in femur and tibia using the device;

FIG. 18 shows a flexion gap optimisation device (FGOD) (instrument 9);

FIG. 19 shows a distal femoral surface block and anterior femur referencing stylus for instrument 9;

FIG. 20 shows the anterior profile of the assembly of instrument 9 in which the FGOD is coupled with a measurement scale and the distal femoral surface block and stylus;

FIG. 22 shows another flexion gap optimisation device (FGOD v. 2, instrument 9);

FIGS. 23a to 23g show a pictorial guide to the use of the flexion gap optimisation device (instrument 9);

FIG. 24a shows another FGOD device (FGOD v.3, instrument 9) with its associated components;

FIG. 24b shows a side view of the FGOD v.3 shown in FIG. 24a;

FIG. 24c shows a schematic representation of the function of the flexion gap optimisation device (FGOD);

FIG. 25 shows a schematic representation of the function of the JLF (instrument 7);

FIG. 26 shows how the pins placed using the JLF device are not affected by the presence of any fixed flexion deformity of the knee joint;

FIG. 27 shows a schematic representation of the centre of the joint gap being identified in extension and the distal femoral resection corresponding to this;

FIG. 28 shows a schematic representation of the arc of motion of the knee;

FIG. 29 shows a schematic representation of the flexion gap;

FIG. 30 shows a schematic representation of the function of the distal femur surface block;

FIG. 31 shows a schematic representation of the function of the FGOD device main component (instrument 9); and FIG. 32 shows a femur only femur only femoral condyle referencing distal femoral resection device.

The components in the drawings are not necessarily to scale, emphasis instead being placed upon illustrating the principles of the teachings herein.

Broadly speaking, prior art knee arthroplasty methods have involved selecting an "off the shelf" prosthesis which is as close as possible in size to the patient's knee, and then fitting this in a prescribed position that observes the theoretical mechanical axis of the limb. The surgical procedure involves resecting (making a bony cut and removing) the joint articular surfaces of the femur and tibia to create planar surfaces which are perpendicular to the longitudinal mechanical axis of the limb. A symmetrical force will then be applied to the prosthesis whilst it is being loaded and this ensures that the prosthesis lasts as long as possible in vivo.

The limitations of this method is that knee joint soft tissue (the ligaments and capsule) do not necessarily move in balanced tension with reference to the notional axes described and so the mechanical placement of the prosthesis results in an imperfect outcome in terms of the interaction between the movement of the knee replacement implant and the soft tissue of the knee. Accordingly, in order to correct this, it is necessary for the surgeon to check the patient's soft tissue, balance and function after implantation and to make adjustments to the soft tissue with soft tissue releases. It is also necessary for the patient to undergo physiotherapy after surgery to bring about adaptation of the soft tissue for it to match the prostheses movement. In order to improve the functional outcome and align the prostheses in accordance with the soft tissue movements, prior art techniques have been developed to use an MRI scan and a custom jig to achieve an anatomical alignment of the prosthesis in each case, but this is expensive and it is still necessary for the surgeon to carry out some soft tissue adjustment.

The knee has a medial and a lateral compartment, which in most people are at different levels. Prior art methods and instruments overlook the differing levels of the joint compartments and measure the resections off one or the other, resulting in a discrepancy between the positioning of the implants on each side of the joint and hence and inaccuracy in the overall prosthesis position. The patella (knee cap) articulates (or moves) against the lateral (outer) femoral condyle (the prominence of the femur in the knee joint). Prior art techniques and instruments position the femoral prosthesis referenced from the more prominent condyle, which is usually the medial (inner). This means the less prominent lateral condyle is typically distalised (advanced further out) with prior art techniques and instruments. This change to the position of the lateral femoral condyle resulting from inaccuracy in the positioning of this aspect of the prosthesis imparts undue tension on the patella. This phenomenon causes tightness in the lateral soft tissue, which sometimes causes pain and limitation to the knee movement as a whole. The invention described seeks to address these inaccuracies by making the distal femoral resection referenced from the lateral femoral condyle (even if less prominent than the medial) in order to optimise the patella-femoral interface. It may also permit adjustment of the femoral prosthesis position in order to accommodate differing medial and lateral joint levels.

In addition, the 'flexion gap' (the dimension of the interval between the posterior femoral resection and the tibial resection that determines soft tissue tension with the knee in a bent position) is dependent on an interaction between the angle with which the tibial resection is made and the size of femoral prosthesis selected. Prior art techniques make a tibial resection independently of the femoral size and given the incremental sizes of the femoral prostheses available in any system, there is an approximation and a compromise in the size of the flexion gap, the posterior femoral offset and the prominence of the femoral prosthesis anteriorly (at the front, against the patella). The compromise reached does not replicate all the parameters accurately in a majority of cases. The invention described links the tibial resection angle with the femoral prosthesis size and position. In this way the invention seeks to satisfy the stated criteria simultaneously and avoid resorting to an undesirable compromise.

Throughout the application the patient's pre-diseased joint line is referred to by terms such as native or original joint line or level. These terms are all used to indicate a position of the knee joint in which the soft tissue has physiologically sound tension, i.e. tension in the soft tissue is balanced and the surgeon feels that the knee is in its natural position.

The order of the steps in the method of the invention may be important to align the prosthetic knee joint to the patient's individual biomechanics. The steps of the method are:

1. Surgical approach to the knee, removal of osteophytes and remodelled peri-articular bone.
2. Insertion of intra-medullary and extra-medullary guide (s) and application of distraction to the joint in extension, demonstrating the spatial relationship between the femur and tibia as guided by the soft tissue. Measurement of the limb coronal alignment and direction of soft tissue releases when required to maintain a coronal alignment within a mechanically acceptable margin.

3. Insertion of joint gap guides and measurement of sizes of gaps—this will also guide any correction of the coronal alignment and determine the position and coronal orientation of the patient's original joint levels (each compartment independently). An adjustment is available to the surgeon for asymmetric wear of the opposing femoral tibial articular surfaces or to account for a difference in the medial and lateral compartment joint levels.
4. Placement of pins from which parallel distal femoral and tibial bony resections may subsequently be referenced for a gap balanced rectangular extension gap centred on the joint level with or without a coronal slope of the joint articulation. An adjustment can be made for fixed flexion deformity (if present).
5. The distal femoral bony resection is made.
6. The re-application of joint distraction in flexion. The flexion gap jig assembly measures the AP dimension of the distal femur and for the selected size of femoral component, can make an adjustment to the sagittal posterior slope of the planned tibial resection for a precise rectangular, balanced flexion gap. Pins are placed in the tibia for the definitive tibial resection (incorporating the sagittal slope adjustment) and also pins in the femur for the femoral anterior and posterior resections.
7. Final femoral finishing block and resections
8. Trial and definitive implantation of prostheses.

In an embodiment the flexion gap may be made before the extension gap if desired or conventional neutral resection(s) may be made in the femur or tibia and gap balanced resection of the other bone performed.

In another embodiment the distal femoral resection and the tibial resections may be made independently according to the mechanical axis of the limb and balance achieved with soft tissue releases. In this case a conventional IM rod placed in the femoral canal determines the femoral axis. The "Femur Only Femoral Condyle Referencing Distal Femoral Resection Device" invention described with reference to FIG. 32 is used to pin for and resect the distal femur measured from one or the other condyle (the lateral is preferred as described earlier) irrespective of which condyle is the more prominent in a particular case.

Advantages of the claimed method over the conventional methods of knee arthroplasty may include:
1. Ability to measure limb coronal alignment in extension with physiological soft tissue envelope tensioning. If required, judicious and directed ligament releases can be performed to maintain a coronal alignment within an acceptable range. Unnecessary ligament releases to modify soft tissue to comply with arbitrary mechanical bony resection are avoided.
2. Resection of the tibia and femur accurately and relative to the original joint level referenced from gap guides in extension and flexion. The lateral or medial joint line can be observed or a sloping joint line incorporating both or a compromise between these considerations using the same instrument.
3. Resection of the tibia and femur parallel to the original joint level, and thus parallel to each other. This means the ligamentous structures between tibia and femur are maintained in balanced and physiological tension in extension and flexion by the subsequent prosthesis implantation, reducing the need for subsequent post-operative soft tissue adaptation by physiotherapy.
4. Optional positioning the prostheses on the tibia and femur to match the coronal alignment and orientation of the articulation of the native individual knee rather than in a generic perpendicular orientation (prior art). The coronal angulation of the articulation can be measured and adjusted if required to maintain it within an acceptable range.
5. Resection of the tibia to match the sagittal posterior slope of the native tibial plateau, however, also with an additional innovative feature to allow adjustment of the sagittal slope to take into account femoral prosthesis size increments, maintaining a consistent ligamentous tension between femur and tibia in flexion by means of accurate flexion gap sizing whilst maintaining optimal anterior femoral prosthesis component position for optimal patella tracking.
6. The application of the above methodology to innovative manual instrumentation and physical devices or computer navigated instrumentation.

Figure 1:
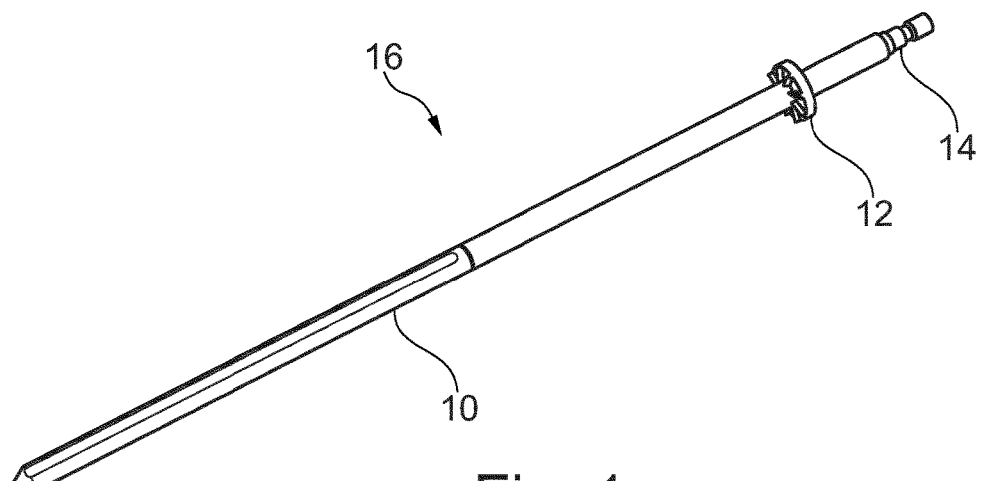
FIG. 1 shows an intramedullary guide mill (instrument 1)

FIG. 1 shows an intramedullary guide starter drill and mill 16 (instrument 1) which can be used for drilling a channel (called a medullary canal) in a bone into which an intramedullary guide can be inserted. The instrument 16 includes an elongate drill piece 10, a handle 14 at a distal end of the drill piece 10, and a mill part 12 between the handle and the drill and extending radially from the drill. The mill is used to make a pit in the end of the bone into which the drill is inserted by twisting the handle of the instrument 16 so that it rotates relative to the bone. The intramedullary drill and mill is used to drill a hole called the medullary canal, a canal lying substantially along the central longitudinal axis of the femur. It may be used to drill a hole along the central longitudinal axis of the tibia also.

Figures 2, 3:
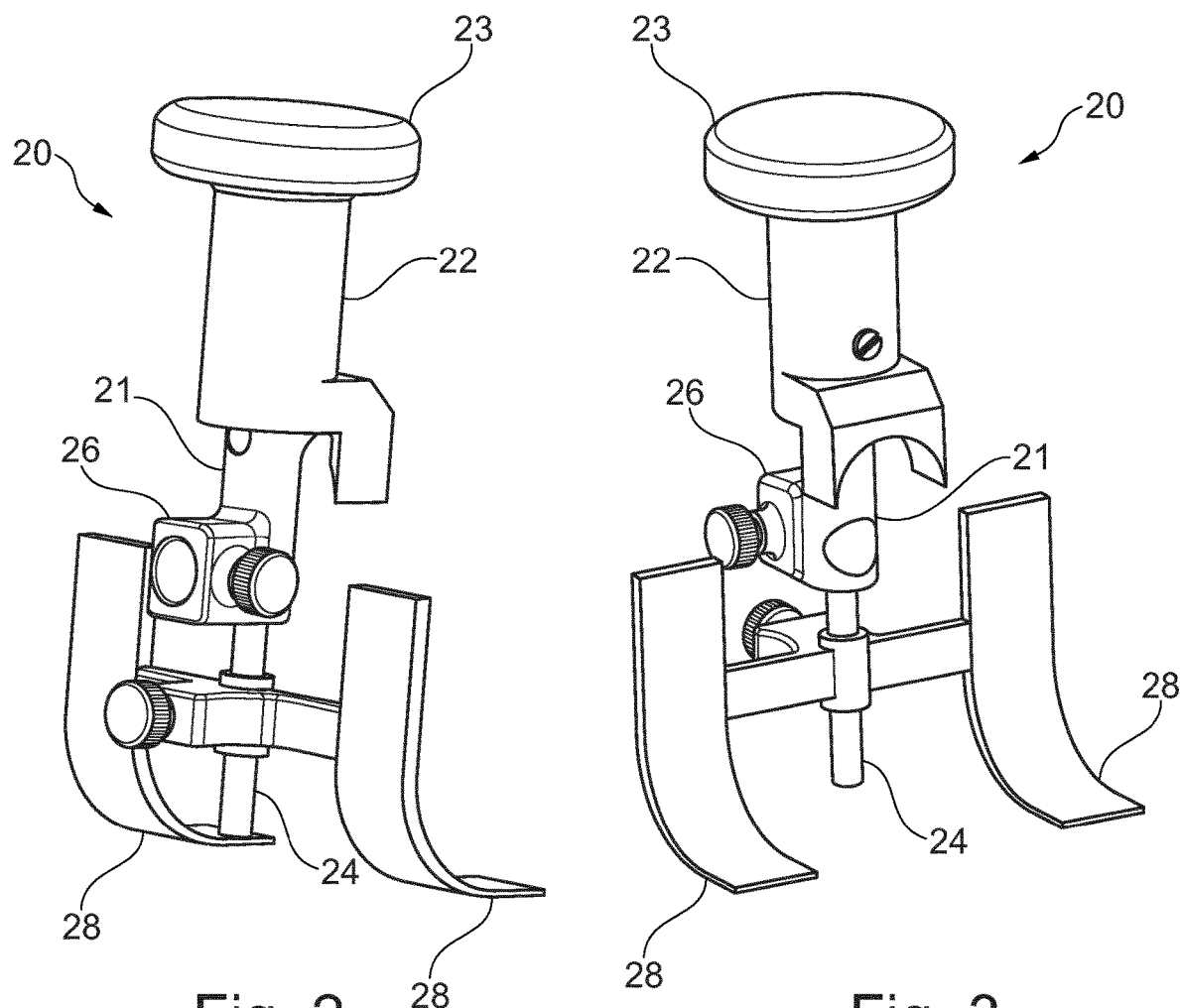
FIG. 2 shows a notch cutter (instrument 2), a bony channel cutting device for the anterior facing projection of an intramedullary guide.
FIG. 3 shows the inner profile (facing the femur) of the notch cutter (instrument 2) of FIG. 2.
Figure 4:
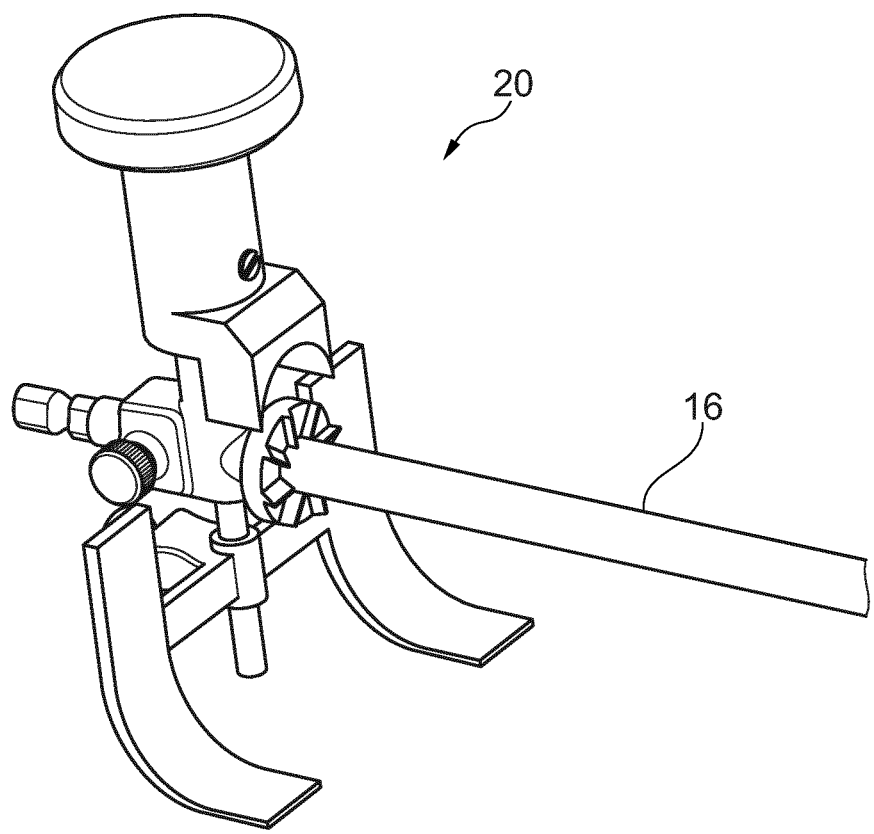
FIG. 4 shows instrument 2 mounted on instrument 1.

FIG. 2 shows a notch cutter 20 (instrument 2) for cutting a bony channel into the end of the bone. The notch cutter 20 comprises a box chisel 22 having a cylindrical strike plate 23 at a first end and a projecting chassis 24 at a second end and a body 21 between the two. The box chisel 22 is spring loaded and attached to the body 21 by a spring located on the body 21 of the instrument. The body of the notch cutter also includes an attachment device 26 for attaching it to the intramedullary guide starter drill and mill 16. At the second end of the instrument a leg supporting member radially extends from around the chassis 24. A pair of curved legs 28 extends from the leg supporting member. In use the legs 28 fit around the femoral condyles to align the notch cutter perpendicular to the condyles and brace it. When the notch cutter is used with the tibia, the legs 28 may be omitted. In use the notch cutter 20 is attached to the intramedullary guide starter drill and mill 16 and the cylindrical plate 23 of the box chisel is struck with a hammer, driving the spring loaded box chisel 22 downwards to remove a block of bone down as far as the cylindrical mill 12 on the intramedullary guide starter drill 16 (instrument 1). FIGS. 3 and 4 show alternative views of the notch cutter 20, FIG. 3 showing the inner profile (femur facing) of the notch cutter and FIG. 4 showing the notch cutter mounted on the intramedullary guide starter drill and mill 16. The notch cutter cuts a channel into the anterior face of the distal end of the femur to the medullary canal. In use this canal accommodates part of the distractor mechanism.

Figure 5:
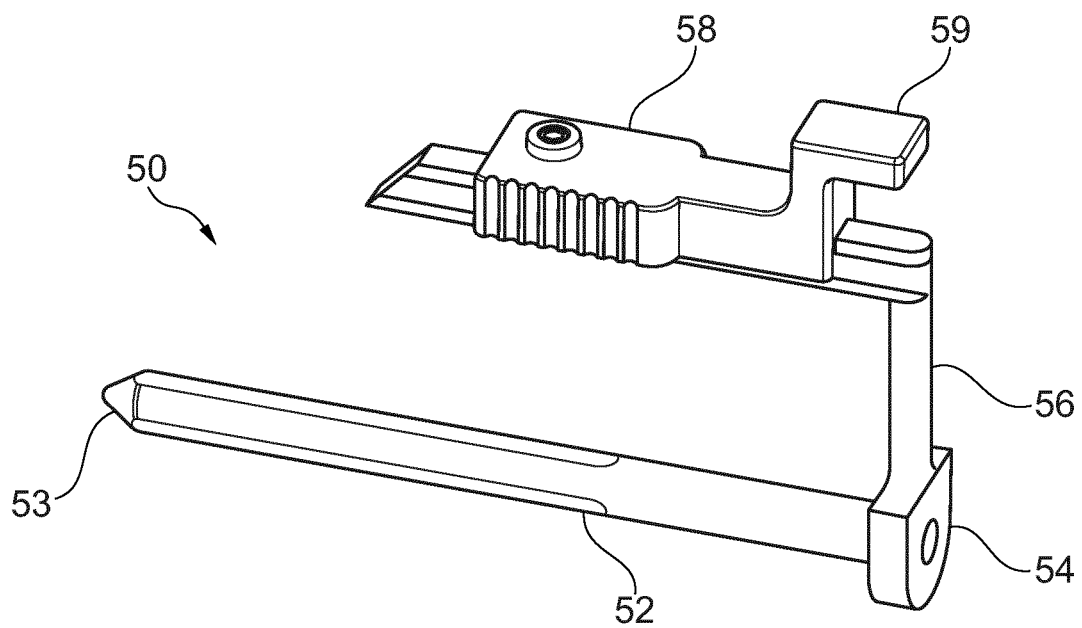
FIG. 5 shows an intramedullary guide (instrument 3)

FIG. 5 shows an intramedullary guide 50 (instrument 3) which can be positioned into the channel created in the femur by the intramedullary guide starter drill and mill 16 and notch cutter 20. The intramedullary guide 50 comprises a pencil like rod 52 having a sharpened tip at a first end 53 and a flat plate 54 radially extending from a second end. The flat plate 54 is attached to a telescopic arm 56 which extends perpendicularly to the rod 52. A second plate 58 extends perpendicularly to the arm 56 and parallel to the rod 52 but spaced apart from the rod 52, so that in use the rod extends within the bone and the second plate 58 lies parallel to the rod 52 but external of the patient's limb. The plate 58 includes a sliding interlock mechanism 59 to which subsequent instruments may be mounted. When the intramedullary guide 50 is inserted into the medullary canal of the bone, the flat plate 54 and arm 56 at the end of the rod 52 lie recessed into the pit in the bone (made by instrument 1) and the bony block (resected by instrument 2).

Providing an intramedullary guide which in use is recessed into the femur (or tibia) enables the knee to be fully extended with the guide in-situ. The guide is inserted by initial drilling and milling of the distal femoral or tibial plateau articular surface aligned with the medullary canal. A bone cutting device, the notch cutter, produces a channel for a perpendicular projecting arm of the guide recessed below the articular surface. The arm in turn leads to a parallel plate lying outside the knee from which the sagittal orientation of the femoral canal according to the intramedullary guide can be referenced. The plate includes an interlocking mechanism for the attachment of subsequent instruments. The guide can function as an anchor for the distraction device. In use part of the distractor device can abut the first plate 54 of the intramedullary guide 50. The guide may be produced in a variety of lengths and diameters for appropriate individual fit.

Figures 6, 8:
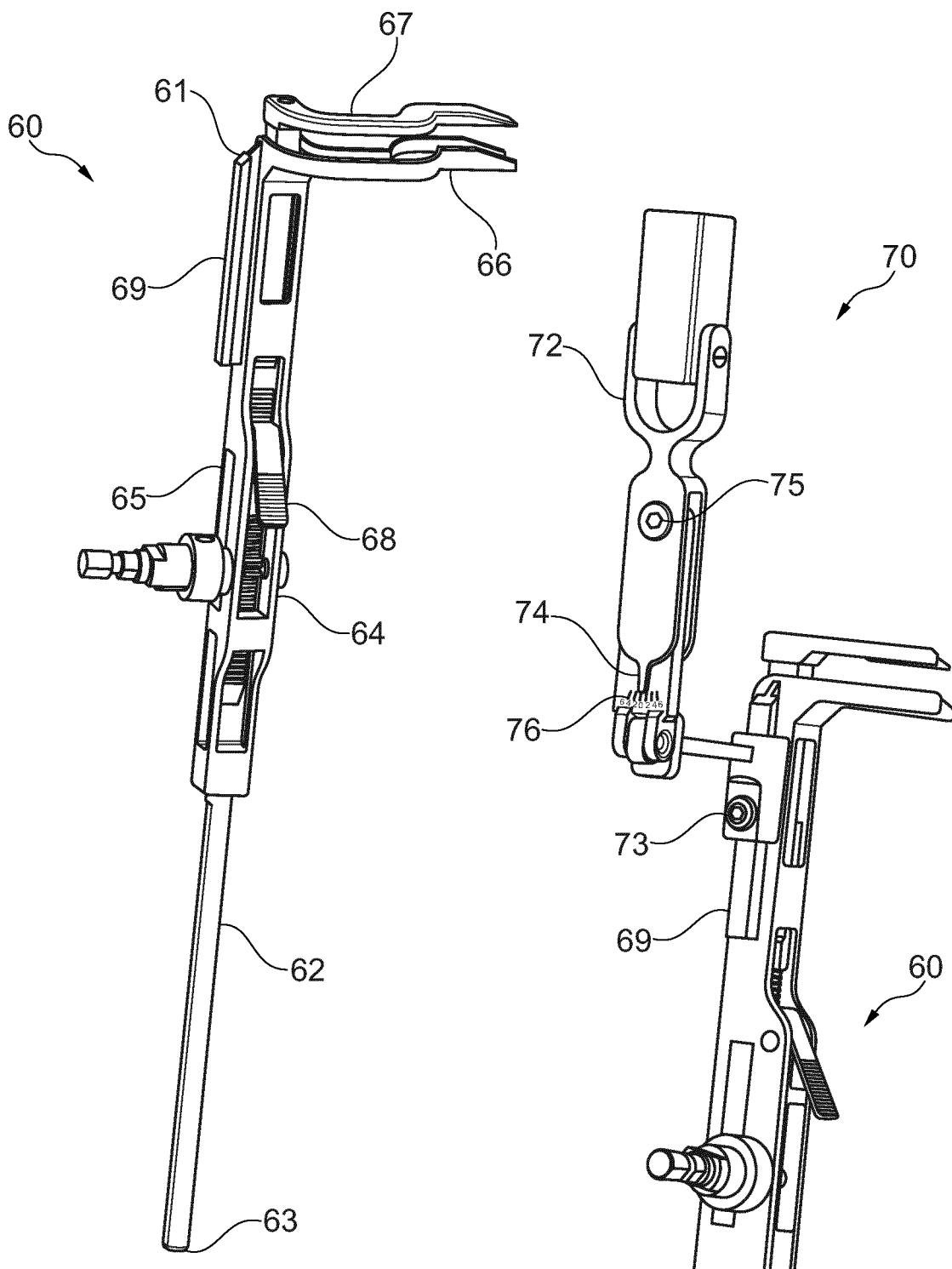
FIG. 6 shows an extramedullary tibial alignment guide and distractor (Instrument 4)
FIG. 8 shows the coronal limb alignment guide of FIG. 7 (instrument 5) mounted on the extramedullary tibial alignment guide and distractor of FIG. 6 (instrument 4)
Figure 16:
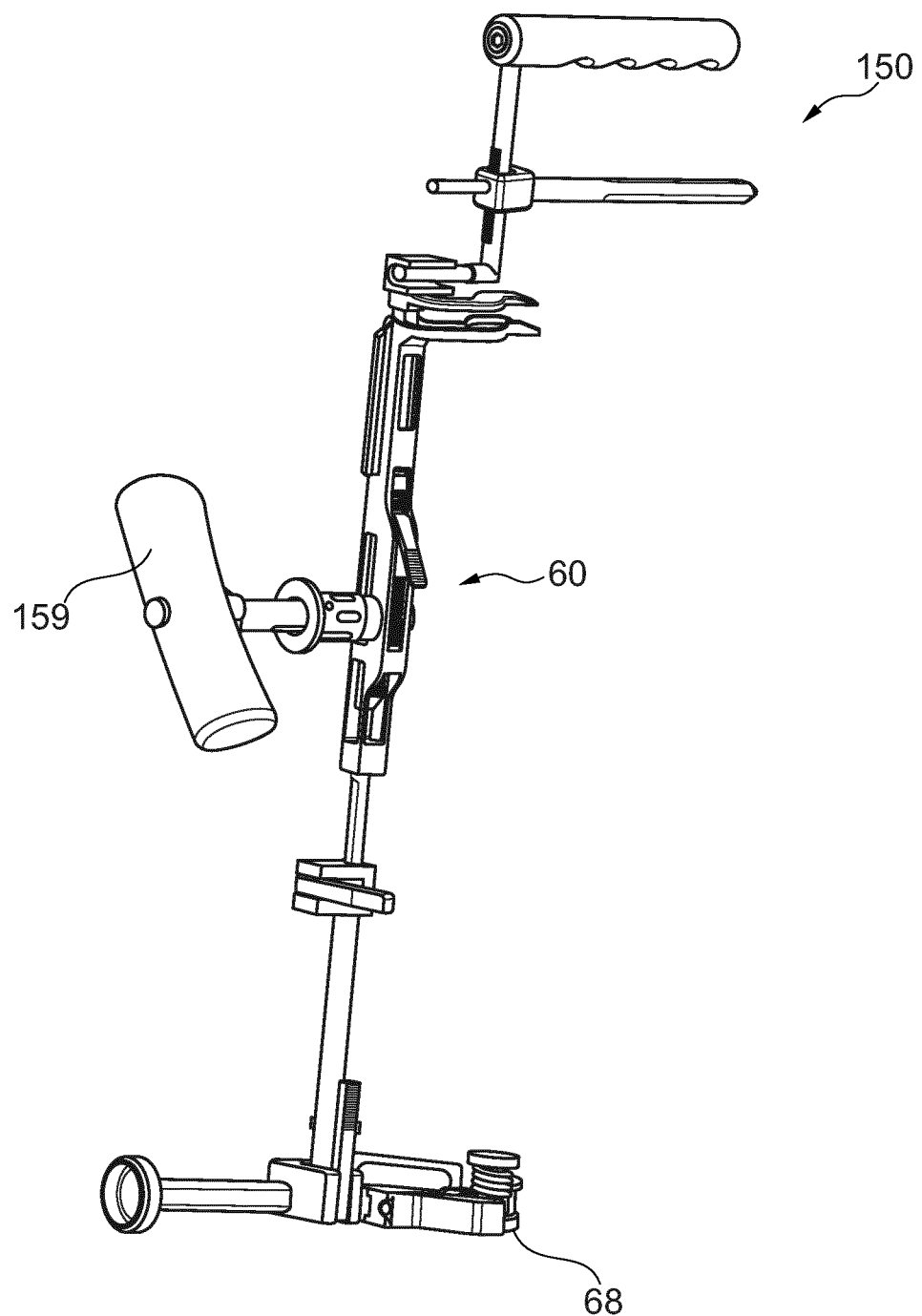
FIG. 16 shows instrument 4 engaged with instrument 8.

FIG. 6 shows an extramedullary tibial alignment guide and distractor 60 including an extramedullary rod 62 having a proximal end 61 and a distal end 63. At the distal end a clamp 68 (as shown in FIG. 16) allows the guide to be attached to the patient's ankle. A distractor 65 is provided about the rod 62 at the proximal end of the rod. The distractor 65 includes a static arm 66 extending perpendicularly to the rod and a movable arm 67 parallel to and proximal of the static arm 66. The static arm 66 can be pinned to the tibial plateau. The movable art 67 is movable relative to the static arm 66 and rod 62. The movable arm 67 is shaped so as to fit into the notch made in the anterior distal femur. In use it contacts the plate 54 of the intramedullary guide 50. Both the static 66 and movable 67 arms are narrow relative to the width of the tibia and femur in the coronal place. In an embodiment the first and second arms of the distractor may be, for example, approximately 5 mm thick by 10 mm wide. Such dimensions should provide enough material to give enough strength to the distractor to separate the joint. Also, arms of this size can fit into the recess and notch cut into the femur, between the tibia and femur. The centre of the tibia may not always be aligned with the centre of the femur. In some embodiments it is important that the first arm of the distractor is in line with the centre of the tibia, so that the extramedullary rod follows the longitudinal axis of the tibia in the coronal plane. So that the distractor can align with the centre of the tibia and also fit into the notch in the distal end of the femur, the notch cut in the femur is larger than the width of the arms of the distractor. For example, the notch, and the plate 54 of the intramedullary rod 50, may be approximately 25 mm wide in the coronal plane.

The distractor includes a rack and pinion mechanism 64 for forcing the movable arm 67 away from the static arm 66; this mechanism maintains the distraction applied between the arms. A release button 68 provided on the rack and pinion mechanism 64 can be depressed to release the distraction force and allow the moveable arm 67 to move back towards the static arm 66. At the proximal end 61 of the extramedullary guide a rail 69 is provided on the anterior surface for attachment to other instruments. In use the static arm 66 is secured on to the tibial plateau centre and the moveable arm 67 abuts the femur either directly or on the surface of instrument 3 or interlocked with instrument 8 (described later) in flexion and applies distraction to the joint. The recessed positioning of the arm 67 and instrument 3 which it abuts allows distraction to be applied in full extension with instrument 3 in-situ.

The incorporation of the distractor mechanism within the extramedullary tibial guide and its engagement with the aforementioned recessed intramedullary femoral guide leads to joint distraction being possible prior to any bony resections being made and specifically without it being necessary for a tibial resection to be made and a plate being applied to the resected tibial surface for distraction. In a further embodiment a plate attachment can be added to 66 for the distractor to engage with the tibia after a bony resection has been made, or in the explanted revision knee arthroplasty application. Distraction can be applied with the femoral and tibial intramedullary and extramedullary guides in-situ. Therefore, gap balanced extension gap resection may be planned and performed as the axes of the tibia and femur can be referenced from the guides whilst the knee is distracted.

The extramedullary guide aligns with the tibia, functioning as a reference for the axis of the tibia. At its distal end, a clamp fits around the ankle. The chassis of the guide is adjustable on the ankle clamp, to be positioned in a central position relative to the tibia in the coronal plane. The height of the extramedullary guide is also adjustable. The static arm 66 is a perpendicular extension at the proximal end of the guide which in use is positioned over a central position of the tibial plateau and secured into place with a screw or an intramedullary rod. As can be seen from the figures the static arm has a curved profile to avoid impingement with the patellar tendon, although this is not an essential feature. In this embodiment the guide can therefore be used with the patella not dislocated in extension or flexion in order to reference the position of the patella in a revision knee arthroplasty application. Furthermore, the static arm 66 is modular and therefore detachable from the main body of the distractor allowing its position to be reversed for a left or right knee and depending on the surgical exposure used. The movable arm 67 may also be modular, although there is no need for either part to be modular and one or both may be fixed.

In another embodiment the distractor mechanism is built into the chassis of the extramedullary guide and functions with a rack and pinion and ratchet mechanism or a screw or a ratchet operated by an external device such as a laminar spreader.

In other embodiments the distractor mechanism may be, for example, a wind-up screw or a worm-drive mechanism. In an embodiment the distraction arm is recessed into the extramedullary guide modular projection and is itself modular. In an embodiment a flat distraction plate or arm can be used in extension to apply distraction against the recessed femoral extension intramedullary guide (instrument 3). In a further embodiment a different distraction arm can be used in flexion. A distractor arm for use in flexion can incorporate an interlock with the flexion femoral intramedullary guide, as described in a later section.

Due to the fact that the distractor can distract the joint in extension with the tibial and femoral guides in-situ, it is possible to measure the coronal alignment of the limb by means of attachment of an angular measuring accessory device as described in a later section.

Prior art describes extramedullary guides that position tibial resection jigs aligned with the axis of the tibia without distraction. Other prior art describe various distractors based on laminar spreader or rack and pinion or screw mechanisms to distract femur and tibia from each other, thereby applying tension to the soft tissue connecting the femur and tibia. Prior art distractors engage the tibia by means of a tibial plate. This means that resection of the tibia must be made before the distractor can be used (therefore, the tibial resection is not gap referenced for accurate resection level nor anatomical and hence not consistent with the coronal and sagittal slopes of the tibial plateau). If a plate is inserted into the joint before tibial resection has been performed, the thickness of the plate would influence the soft tissue tension, holding the leg in a position different from the patient's original arrangement. The prior art also cannot apply distraction with the intramedullary or extramedullary femoral and tibial guides in-situ and hence a rectangular gap balanced extension gap resection may not be performed as the sagittal orientation of the femur and/or tibia cannot otherwise be determined and the necessary adjustment for any fixed flexion deformity made.

Figure 7:
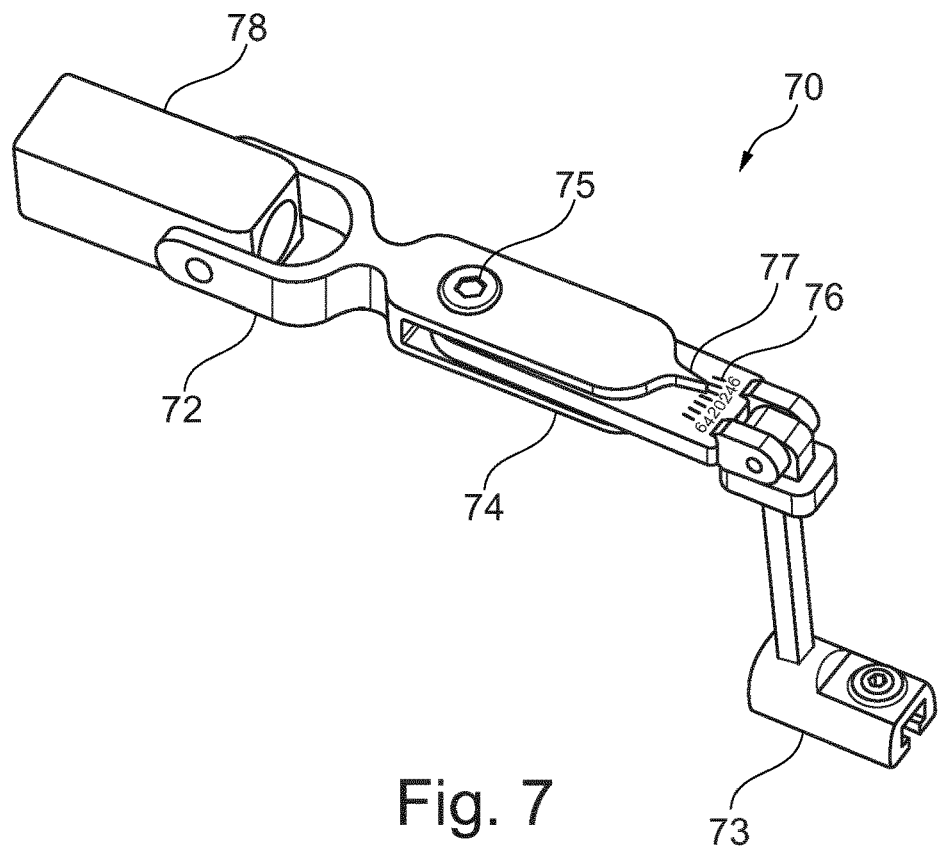
FIG. 7 shows a coronal limb alignment guide (instrument 5)

FIG. 7 shows a coronal limb alignment guide 70, an angular measure which displays the coronal angle of the limb. The alignment guide 70 comprises a first part 72 and a second part 74 which can pivot relative to one another about a pivot point 75. The second part of the alignment guide comprises an attachment part 73 for attachment to the rail 69 of the extramedullary tibial alignment guide and distractor 60 and alignment gauge markings 76. The first part 72 comprises a gauge pointer 77 for indicating the relative positions of the first and second parts against the gauge markings 76 on the second part, and a rod holder 78 for attaching to a rod. The second part 74 of the alignment guide 70 is fixed to the extramedullary tibial alignment guide 60 and therefore aligned with the longitudinal axis of the tibia, whilst the first part 72 is free to pivot about the second part 74. The rod holder 78 of the first part 72 may be attached to a rod which extends to the patient's hip (as palpated by the surgeon or referenced from the anterior superior iliac spine or with x-ray control) and can be moved to align the first part 72 with the patient's femur. When the rod and first part 72 of the alignment guide are aligned with the femur and the second part of the alignment guide is aligned with the tibia the alignment gauge 76 shows the angle between the mechanical axes of the two bones. This angle is known as the coronal angle of the limb. If the measured angle is outside of acceptable limits the surgeon may need to make releases to the soft tissue in order to move the coronal alignment of the limb back into the acceptable range. The coronal limb alignment guide 70 is attached to the extramedullary tibial alignment guide to determine the coronal angle, adjustments are made as required, and then the guide is removed. FIG. 8 shows the coronal limb alignment guide mounted on the extramedullary tibial alignment guide and distractor 60. Of course the gauge pointer may be provided on the second part 74 and the gauge markings on the first part 72 of the alignment guide 70.

Figure 9:
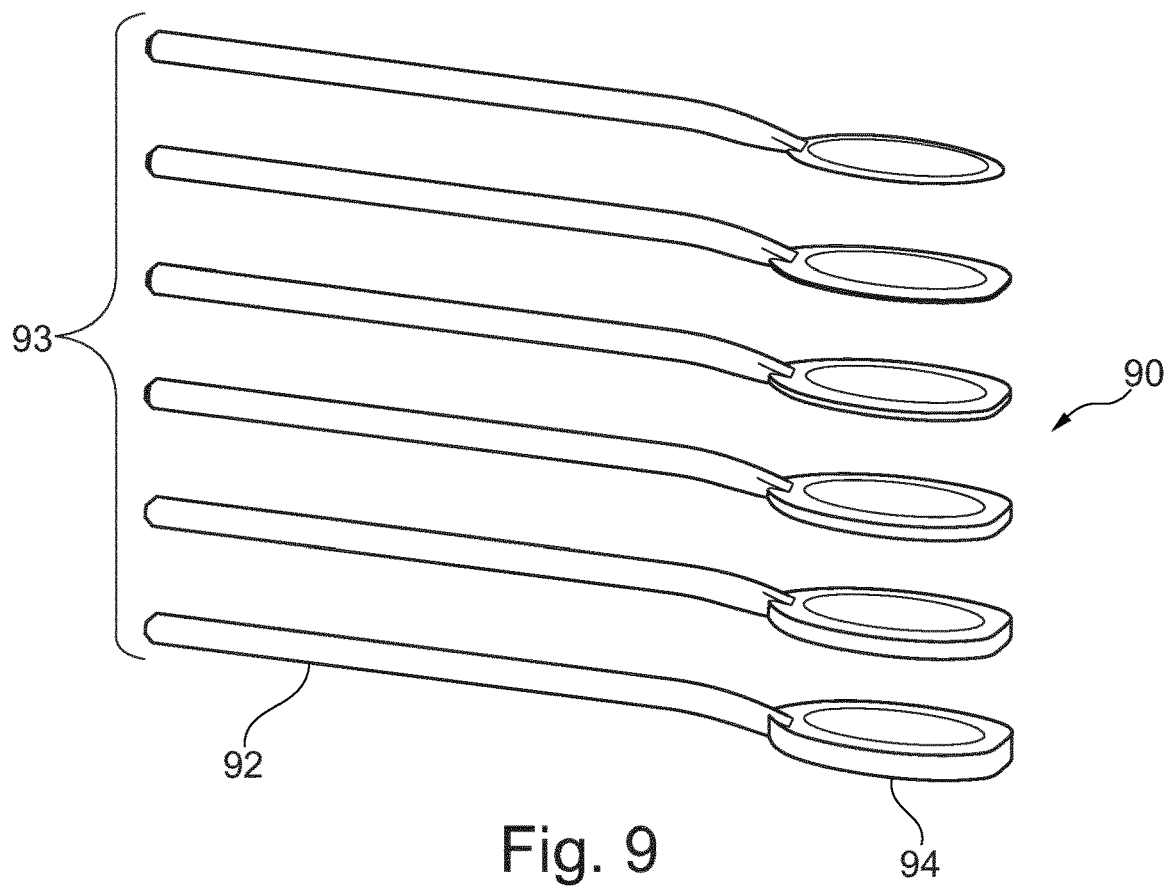
FIG. 9 shows a range of joint gap guides (instrument 6)

FIG. 9 shows joint gap guides 90 for use with a joint level finder (described later). The joint gap guides 90 each comprise an elongate stem 92 extending from one end of a generally oval body 94. A selection of incrementally sized joint gap guides would be provided to the surgeon for use in a knee replacement operation. The stems 92 are generally cylindrical but have one or more flat surfaces 93 on one or more aspects to prevent rotation of the joint gap guide relative to the carrier on the joint level finder. The stem lies in a plane that is offset from but generally parallel to the plane of the body. This arrangement allows the joint gap guides to be used whilst the leg is in extension without impingement of the stem on the femoral condyles or the tibial plateau anterior rim. The joint gap guides are convex on the lower surface and concave on the upper surface (ie: spoon shaped). This shape corresponds to the contours of the surfaces of the femur and tibia and allows them to be inserted in to the similarly shaped spaces between the femoral condyles and the tibial plateau. One joint gap guide is inserted between the tibial plateau and the medial condyle and another between the tibial plateau and the lateral condyle. The joint gap guides have a hole in the middle for the press-fit attachment of augments to increase their thickness on one side or the other side in situations in which the cartilage loss from the femur and tibia are unequal, or cases in which there is also erosion of bone as well as cartilage and the space between the tibia and femur is greater than the largest joint gap guide in the kit. The augments are disc shaped with a small peg on one side for attachment to the hole in the joint gap guides and hence increase the thickness of the joint gap guide on one or the other surface.

The joint gap guides may be generally disc-shaped. In other embodiments the joint gap guides may be another shape such as generally circular, square or rectangular. The guides may have a first side that is convex and a second side that is concave. The stems of the guides may lie in the same plane as the main body.

In use the surgeon would select the appropriate thickness joint gap guide for insertion into the space between the femur and tibia in each compartment of the knee with the knee joint distracted. If the selected guide is too big or too small an alternative one may be tried until the correct fit is found. The surgery would be carried out for conditions of the knee that involve the wearing away and loss of cartilage from the surfaces of the joint. When the knee is distracted a gap therefore appears between the femur and tibia. The corresponding thickness joint gap guide is inserted into this space in each compartment of the knee to determine the location of the pre-diseased interface between the femur and tibia and subsequent positioning of the knee replacement prosthesis to correspond to the same and hence be consistent with the natural knee movement.

Figure 10:
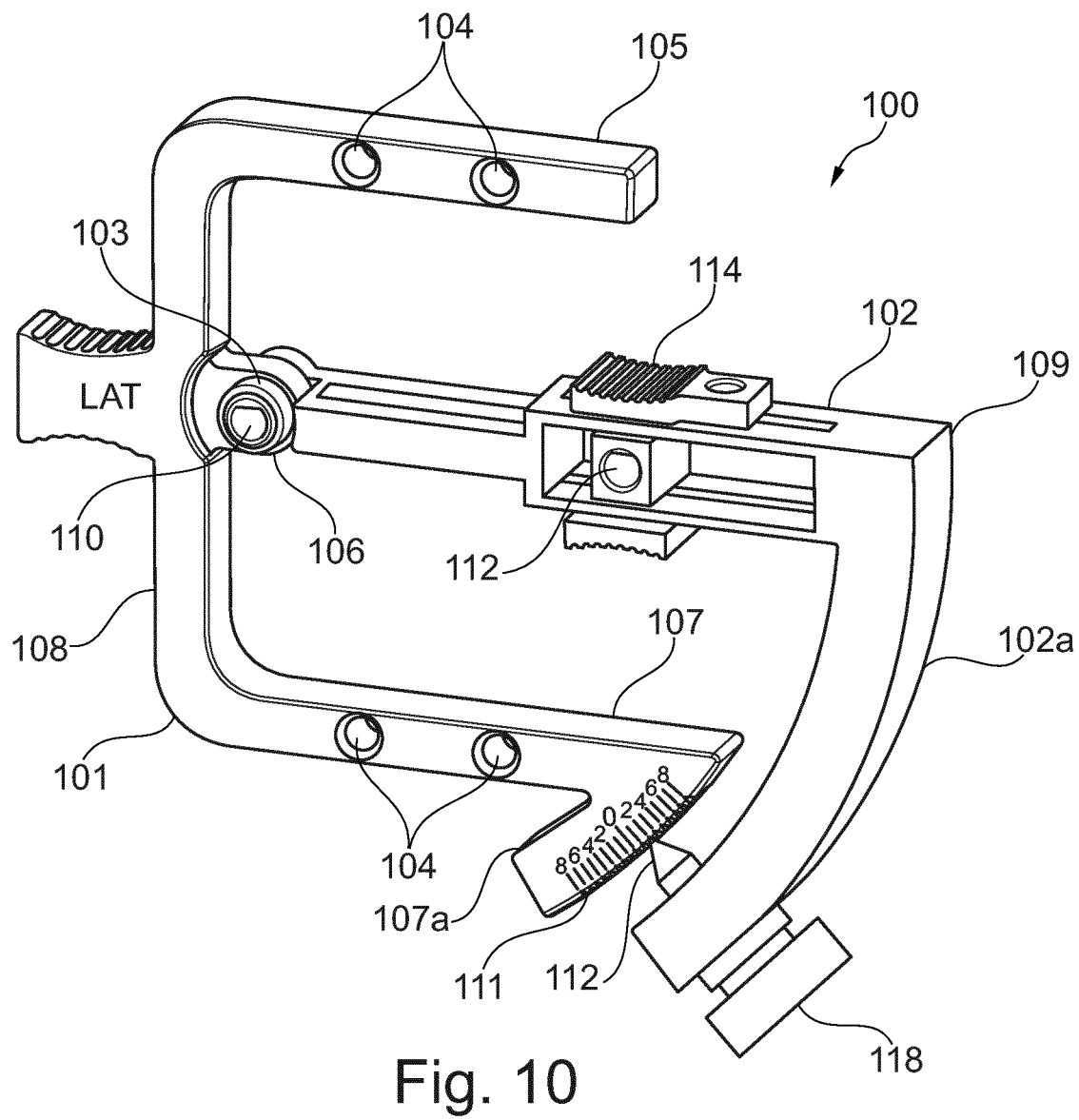
FIG. 10 shows a joint level finder (JLF) device (instrument 7)

FIG. 10 shows a first embodiment of a joint level finder 100 (JLF) device having a first arm 102 and a second arm 101 pivotable relative to one another about a pivot point 103. The second arm is generally C-shaped having a first end 105 and second end 107 and a central portion 108. The first end and the second end extend generally parallel to one another and the central portion extends between the two. An extension 107a of the second end 107 of the second arm includes a gauge scale 111. The first and second ends include holes 104 through which a pinning block accessory may be inserted so as to attach it to the joint level finder. The first arm 102 has a first end 106 and a second end 109. The first end 106 of the first arm 102 is joined to the middle of the central portion 108 of the second arm 101 by a pivot joint 103 such that the angle of the first and second ends of the first arm can be adjusted relative to the angle of the second arm. The first arm 102 extends from its first end 106 in a straight line between the first and second ends of the second arm, an extension 102a of the first arm then curves down from the second end 109 towards and alongside the extension of the second end 107 of the second arm. The extension of the second end 109 of the first arm includes a pointer 112 for aligning with the gauge scale 111 such that the extensions 102a and 107a of the second end of the first arm 102 and the second end 107 of the second arm provide a gauge showing the orientation of the first arm relative to the second arm. The first and second arms can be locked relative to one another by a locking member 118 provided on the extension 102a of the first arm 102. The first arm 102 includes a first carrier hole 110 (lateral carrier hole) for receiving a joint gap guide at the pivot point 103 between the first and second arms. A second carrier hole 112 (medial carrier hole) for receiving a joint gap guide is also provided on the first arm 102, spaced from the first carrier hole 110. The first arm includes an adjustable member 114 portion which allows the second carrier hole 112 to be moved towards or away from the first carrier hole 110. This allows the joint gap guides to be moved closer together or further apart depending on the size of the patient. The joint level finder may include an interlock between the first and second carriers for the joint gap guides is provided a slot 116 which can be used to attach the joint level finder to a mount (the interlock) which in turn attaches to the rail 69 on the extramedullary tibial guide or to an intramedullary tibial or femoral guide.

Where the stems of the joint gap guides lie in a plane that is offset from but generally parallel to the plane of their body, the joint level finder may include an offset such that it indicates the actual position of the line between the centres of the joint gap guides, rather than a line offset from that line.

Optimal knee arthroplasty function is partly dependent on the prosthesis being located at the native or pre-diseased joint level. According to the present invention the joint level is methodically observed at each compartment equally by positioning an appropriately sized joint gap guide in each compartment to secure the knee in its native position. The joint gap guides are attached to the JLF instrument prior to its insertion into the exposed knee articulation in the extended position. The JGGs orientate the JLF to indicate to the position original or native of the knee articulation relative to the longitudinal axis of the tibia or the femur.

The joint level finder (JLF) has a mount section which is fixed relative to the tibial axis and a guide section which is moveable so as to align with the position of the two joint gap guides. As one joint gap guide will be located in each of the joint compartments, the first arm 102 will be aligned with a line joining the centres of the two joint gap guides. This will correspond to the slope of the native or original joint articulation in the coronal plane, forming an angle relative to the axis of the tibia. Following the placement of pins for cutting blocks with the JLF the bony resections can then be made to be parallel with the coronal 'slope' that the two native joint levels form relative to the tibial axis and thus the joint level at each compartment is reproduced by the prosthesis. It is possible for the surgeon using adjustment of the extension 102a, 107a of the ends of the first and second arms of the locking member 118 to vary the position of the first arm 101 relative to the second arm 102 by pivoting it around 103 to modify the orientation of arm 101 to suit the particular situation.

Once the intended resection slope has been determined, pinning blocks are attached to the JLF using holes 104, pins placed in the tibia and femur in turn and the JLF can then be removed from the tibial extramedullary guide and distractor. Distraction can also be released. The knee can then be flexed to permit access as is standard practice and cutting blocks can be placed on the pins before a distal femoral bony resection is made. The tibial pins are retained and in the described technique are provisional at this stage. This is because the pins placed in extension are referenced from the level of the articulation between tibia and femur in extension which is anterior on the tibial joint surface. In flexion the level of the articulation is more posterior and also at a lower level. The tibial resection will be made later in the procedure once the level of the articulation in flexion has also been determined using the flexion gap optimisation device (FGOD) described later.

The JLF is used in extension for the surgical method described, but in a further embodiment could be used in flexion for a flexion gap first technique.

In a further embodiment there is the facility to measure the coronal angulation of the joint line and permit adjustment to bring the slope introduced into the prosthesis position to within an acceptable margin, if the particular knee happens to have very different joint levels in each compartment. In a yet further embodiment the surgeon may observe that wear is asymmetric between the two opposing surfaces of the same compartment. In this case, a further adjustment can be made by the selection of the appropriate sized joint gap guide and its translation by the surgeon towards the less worn side by the attachment of augments.

In the embodiment of FIG. 10 the lateral guide (first carrier hole) is fixed and the medial guide (second carrier hole) can be translated from medial to lateral for the width of knee. In further embodiments the JLF can be reversed for left or right knee or dependent on whether the lateral or the medial compartment is being used as the anchor.

The gap guide carriers 110, 112 shown in FIG. 10 are generally circular but have a flat surface corresponding to the flat surfaces of the gap guide stems for rotational stability of the gap guide relative to the joint level finder, however this is not essential. In another embodiment the JLF can be interlocked in extension with instrument 4 or instrument 3 to hold it parallel with the sagittal axis of the tibia or femur respectively. This means the JLF can place pins for the tibial and distal femoral resections for a gap balanced rectangular extension gap with distraction applied and gap guides in-situ to center the extension gap at the true pre-disease (native or original) joint line.

In a yet further embodiment, as the tibial and femoral sagittal axes are referenced in turn by the JLF, with the gap guides being the point of reference, fixed flexion deformity of the knee can be accommodated. The extension gap is made appropriate for the anticipated full extension to be achieved subsequently when posterior capsular release is made.

In a yet further embodiment the JLF can function to introduce a measured amount of coronal slope to the joint line to accommodate individual anatomy. The JLF assumes a position perpendicular to the tibial axis when engaged in the interlock with instrument 4. In this case the mobile arm of the JLF device orientates with the joint gap guides to align with and display on a scale the angular measurement of the anatomical slope that is present. The surgeon can then optionally adjust the JLF device to introduce the appropriate slope guided by the display up to an accepted limit. Such an adjustment may be desirable in some cases in order to align the implants to a more reasonable compromise between biomechanical considerations and symmetrical loading. The surgeon angles the pinning arm relative to the main chassis by matching the number on the dial of the pinning arm to the number on the dial on the JLF chassis.

Prior art references the native joint level from the existing worn surfaces of the femur and tibia. However, the existing worn joint level will be irregular due to the arthritic disease process. Prior art for TKR uses either a stylus placed against a certain point (the highest or lowest) of the tibial plateau or a flat surface placed against the femoral condyle distal surface to identify the joint level and reference from it. These methods are necessarily approximations and can only be applied to one of the two knee compartments at any one time. Thus the prior art references the joint level from one of the two compartments only and assumes the other to be alongside but in fact the two compartments usually articulate at different levels. Thus the prior art can be subject to a significant inaccuracy.

Figure 11:
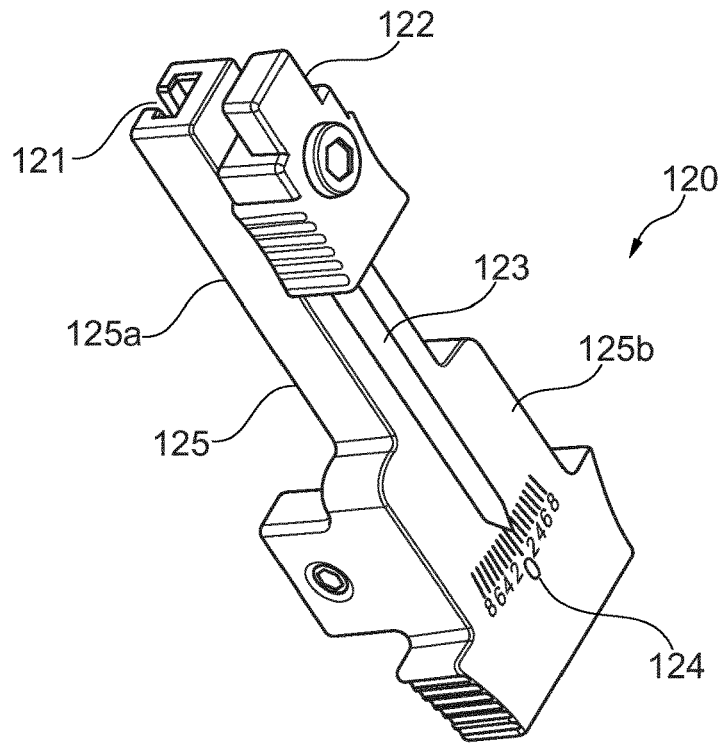
FIG. 11 shows an interlock for mounting between the extramedullary tibial alignment guide and distractor, and the JLF (instruments 4 and 7) incorporating an angular measure display.
Figure 12:
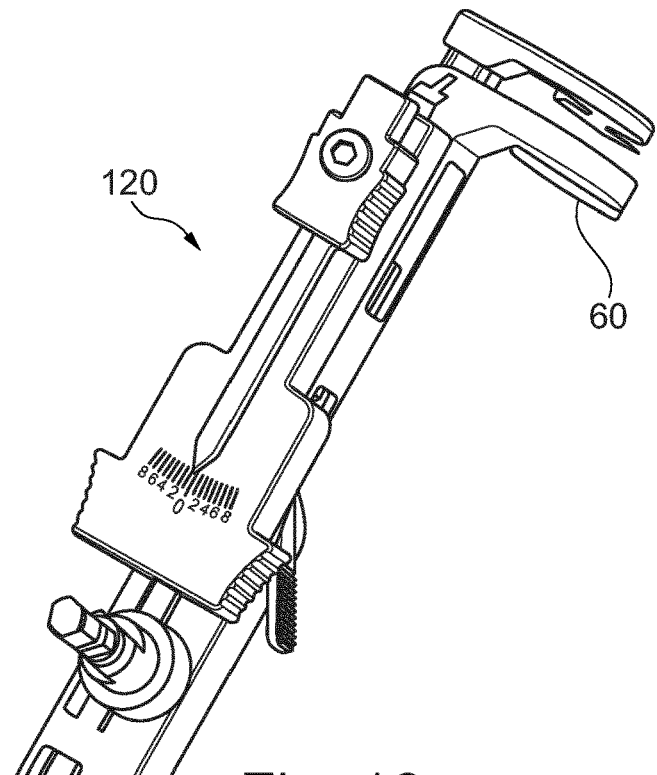
FIG. 12 shows the interlock of FIG. 11 mounted on the extramedullary tibial alignment guide and distractor (instrument 4)
Figure 13:
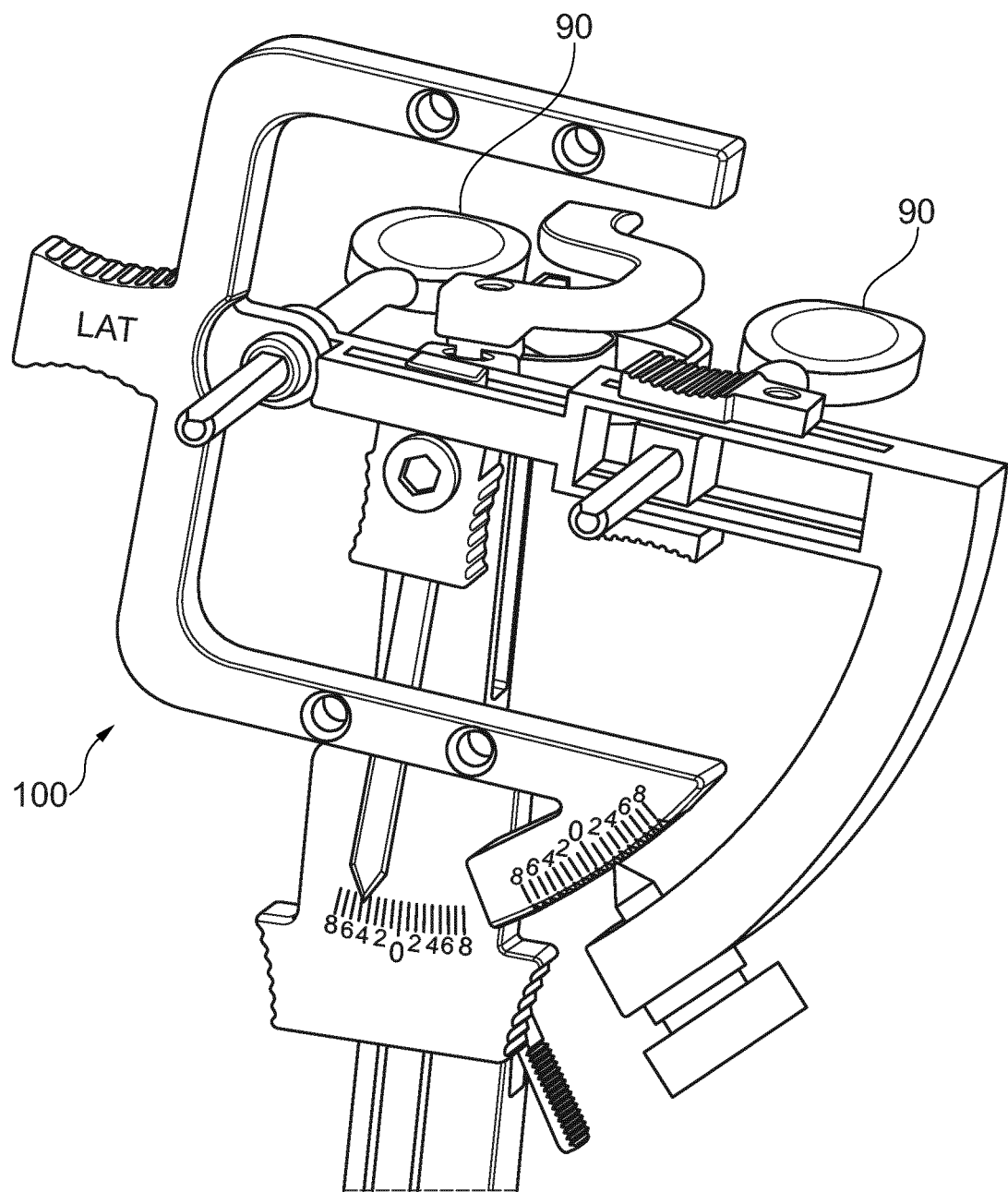
FIG. 13 shows the JLF of FIG. 10 (instrument 7) mounted on the extramedullary tibial alignment guide and distractor (instrument 4) with the interlock/angular display engaged and joint gap guides in-situ in extension.

FIG. 11 shows the interlock 120 for joining the extramedullary tibial alignment guide and distractor 60 and the joint level finder 100. The interlock 120 comprises a main body 125 having first 125a and second 125b faces and including a rail attachment feature 121 on the first face 125a and a gauge dial 124 on the second face. The interlock can attach to the rail 69 of the extramedullary guide 60 by the rail attachment feature. The interlock includes a notch 122 on the second face 125b for fitting into the slot 116 on the first arm 102 of the joint level finder. The notch is pivotable relative to the main body 125 of the interlock so that it can move with the joint level finder. The notch is attached to a gauge pin 123 which indicates on the gauge 124 the relative orientation of the joint level finder to the rail of the extramedullary guide and therefore to the axis of the tibia. FIG. 12 shows the interlock 120 mounted onto the extramedullary guide. FIG. 13 shows the joint level finder 100 mounted on the extramedullary guide and distractor 60 via the interlock 120, and shows the joint gap guides 90 insitu through the carriers in the joint level finder.

Figure 14:
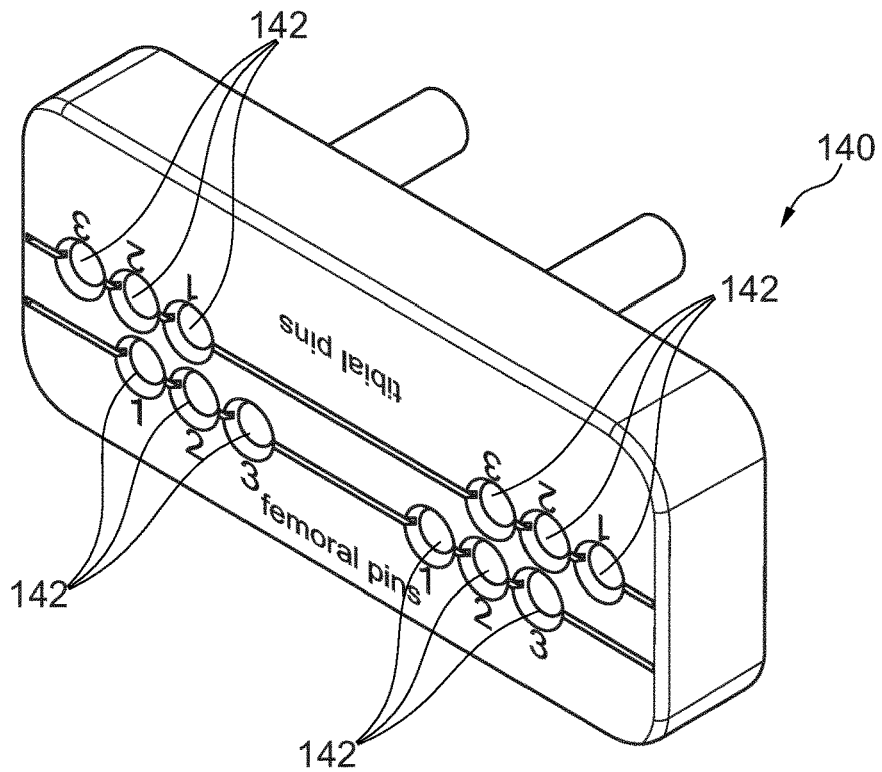
FIG. 14 shows a pinning block accessory for a JLF.

FIG. 14 shows a pinning block accessory 140 for mounting to the joint level finder. The block can be used in a first orientation for pinning the femur and in a second orientation, rotated by 180 degrees, for pinning the tibia. The block 140 has a number of holes 142 spaced apart along two parallel lines through which pins may be placed and driven into the bones. The pins provide a location for cutting blocks to be mounted to the bone subsequently. Two pins are used for each resection. A number of holes are provided to suit individual knee size. To maintain a specific distance between the pairs of pins, they are numbered so that the surgeon will use a pair of pins at the correct distance apart for the holes in the cutting block to correspond.

Figure 15:
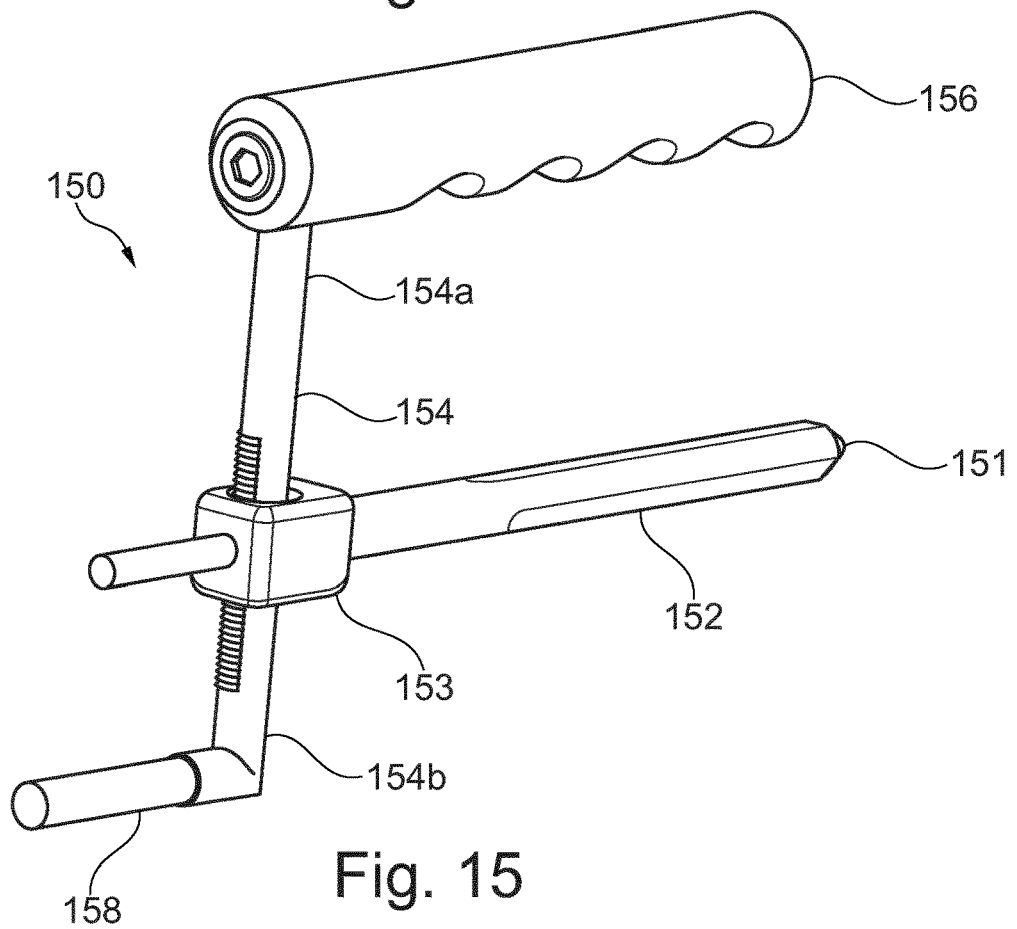
FIG. 15 shows a flexion femoral intramedullary guide (instrument 8)

FIG. 15 shows a femoral intramedullary guide 150 (instrument 8) for use in flexion of the knee. The femoral intramedullary guide 150 includes a pencil shaped elongate rode 152 having a pointed proximal end 151 and at its distal end 153 an arm 154 having first 154a and second 154b ends and extending perpendicularly to the rod 152. At the first end of the arm 154 a handle 156 extends perpendicularly to the arm 154 and parallel to the rod 152. The handle is shaped so as to be comfortable to grip as in use the surgeon may use the handle to offload the weight of the thigh whilst operating the distractor with the other hand. At the second end 154b of the arm 154, the second end extending away from the rod on the opposite side of the rod from the first end, a projection 158 is provided for engaging the distractor. In use the projection 158 extends away from the patient's knee along a line that is parallel to the elongate rod 152. FIG. 16 shows the distractor engaged with the flexion femoral intramedullary guide 150. One method of attaching the projection 158 to the distractor moving arm is a slot facing to one side on the distractor moving arm into which the projection 158 slots into with a rotation movement from the side. Alternatively the connection can be made by a number of other methods of interlocking. A handle 159 is attached to the distractor mechanism to activate the rack and pinion mechanism to separate the first and second arms of the distractor. The handle may be removed once the distraction has been applied, so that it does not hinder the surgeon during the remainder of the procedure.

Following distal femoral resection, the intramedullary guide is placed in the femur in flexion; the guide interlocks with the flexion arm of the distractor. The femoral intramedullary guide 150 for use in flexion incorporates a handle 156 for the surgeon to offload the weight of the thigh off the knee, whilst simultaneously holding the handle of the tibial distractor with the other hand and bringing the knee into a 90 degree angle as indicated by the interlock engaging. Thus the knee is held accurately for flexion gap planning.

FIGS. 17a to 17f show another joint level finder device 170. The joint level finder comprises a mount 171 and a first arm 172 pivotally attached to the mount 171 about a pivot point 173. The mount is generally U-shaped having a first end portion 171a and a second end portion 171b and a central portion 171c joining the first and second end portions. The first and second end portions extend generally parallel to one another, although the second end portion is curved such that it is bowed outwards away from the first end portion. The central portion 171c of the mount includes a slot 186 which can be used to attach the joint level finder to an extramedullary tibial guide.

The first arm 172 has first and second ends and is pivotally attached at its first end to the first end of the mount about pivot point 173 and extends towards the second end of the first arm. The first arm 172 includes a first carrier hole 180 for receiving a joint gap guide and a second carrier hole 182 for receiving a joint gap guide, the first carrier hole being provided through the first arm at the pivot point between the first arm and the mount and the second carrier hole 182 being provided at a location spaced along the first arm 172 from the first carrier hole 180. The first arm includes an adjustable member 184 which allows the second carrier hole 182 for the joint gap guide to be moved towards or away from the first carrier hole. As described before this allows the joint gap guides to be moved closer together or further apart depending on the size of the patient.

The second end 171b of the mount 171 is slightly curved. The second end of the first arm is attachable to the second end of the mount and moveable along the second end 171b of the mount. The second end of the mount is provided with a gauge scale which allows the relative position of the two arms to be measured and read by the user. The two arms may be locked together by locking screw 188 when required.

In an embodiment the joint level finder includes pinning arm angular adjustment member 175 (a second arm) which is a generally elongate member comprising first 175a and second 175b parts and including a hole 180a for passing over a joint gap guide which aligns with the first carrier hole 180 at the first end of the first arm of the joint level finder. The first part 175a of the pinning arm angular adjustment component 175 attaches to the first end of the mount of the joint level finder by a protrusion on the pinning arm angular adjustment component which fits into a corresponding hole on the first end of the first arm by a pressure pin fit. The second part of the pinning arm angular adjustment component 175b is able to pivot relative to the first part of 175a of the pinning arm 175 and relative to the first arm of the JLF about the hole 180a. The pinning arm angular adjustment member 175 includes at its first end, a first side of the pivot hole 180a, a first set of holes 174a for connection to a pin receiver guide and towards it's second end, the other side of the pivot hole 180a, a second set of holes 174b for connection to a second pin guide receiver. The pinning arm angular adjustment component 175 also includes a gauge and mechanism 186 for adjusting the angle of the generally elongate pinning arm angular adjustment component 175 relative to the mount 171 of the joint level finder and therefore relative to the axis of the extramurally rod attached to the tibia or femur to which the JLF is mounted.

As the pinning arm angular adjustment member 175 pivots about the hole 180a the orientation of the holes 174a and 174b for the pin guide receivers is adjusted relative to the axis of the tibia or femur.

In use the joint gap guides are mounted onto the JLF, the assembly inserted into the knee and the joint level finder is fixed into position on the tibial extramedullary guide and distractor mechanism. The mount of the joint level finder is fixed in position relative to the tibial extramedullary guide, whereas the first arm is movable relative to the first arm to align with the position of the joint gap guides and therefore to show the patient's native and original joint line. The angle between the mount and first arm of the joint level finder can be read and the angle of the pinning arm angular adjustment component 175 can be adjusted to align with the measured angle or a lesser angle (but in the direction of the anatomical one) for an appropriate compromise if the measured angle indicates an anatomical angle that is excessive for satisfactory implant loading. The reason the surgeon may decide to offset the line of the pins from a line parallel to the pre-diseased joint line is that the pre-diseased joint line may be too steep to be compatible with the prosthesis. If greater than ±5 degrees, for example, forces on the implant during use of the knee may shear the implant from the bone. Therefore the surgeon may reduce the angle of the line between the pins (and therefore of the cut to the bones) such that it is less than ±5 degrees relative to the axis of the tibia or femur.

Figure 17A:
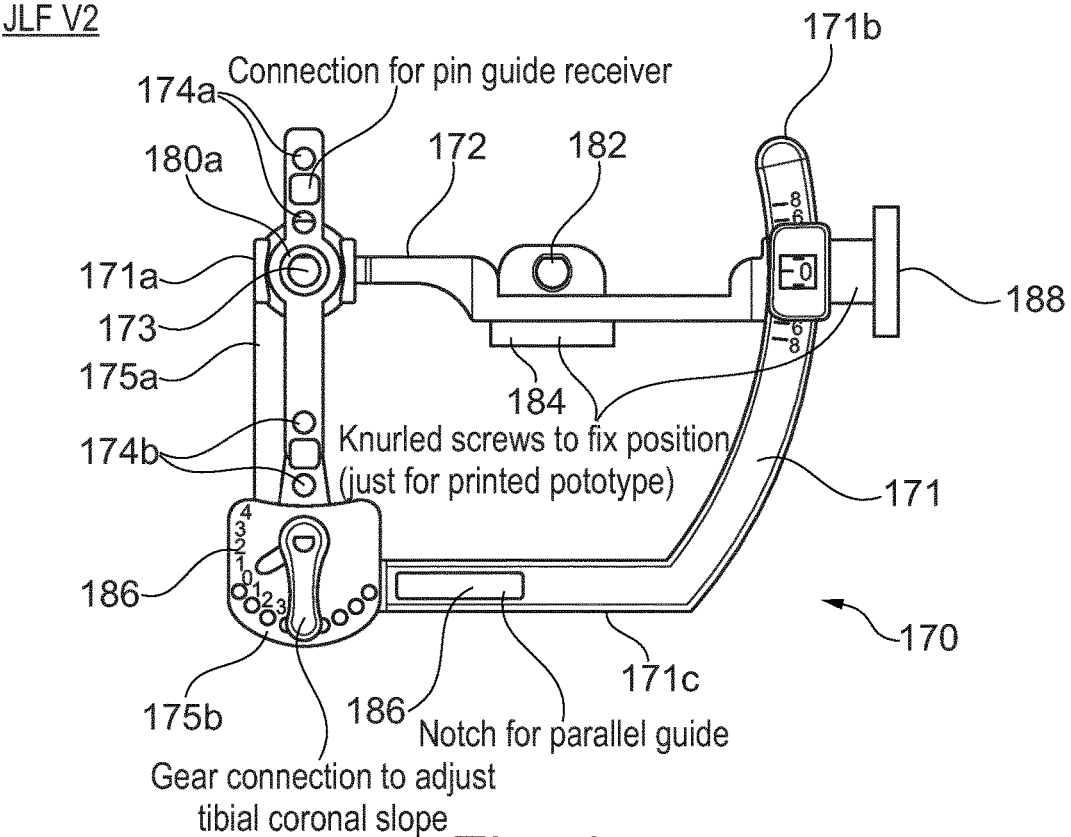
Figure 17B:
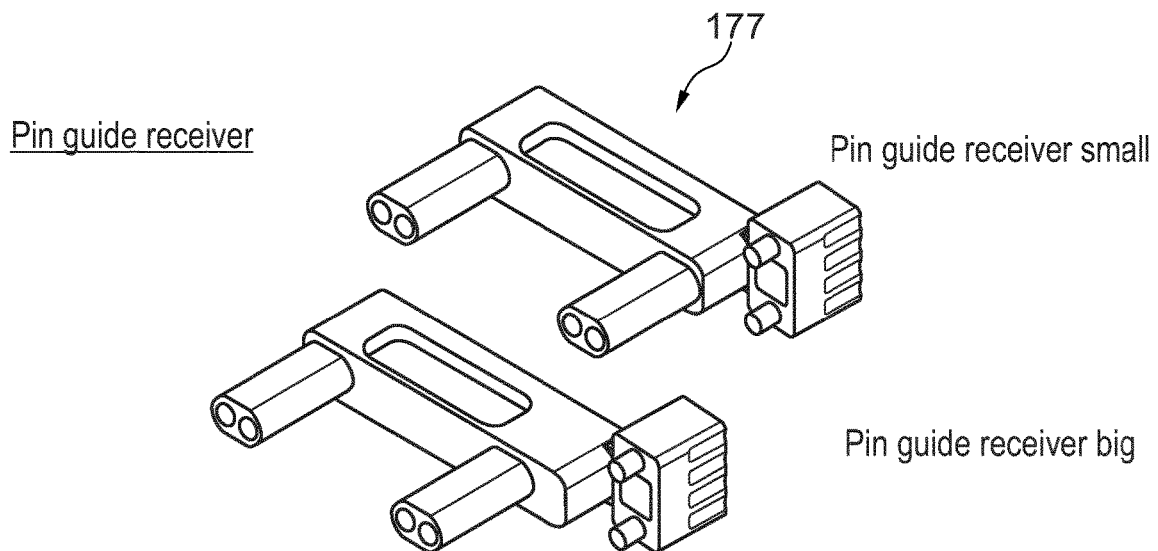
Figure 17C:
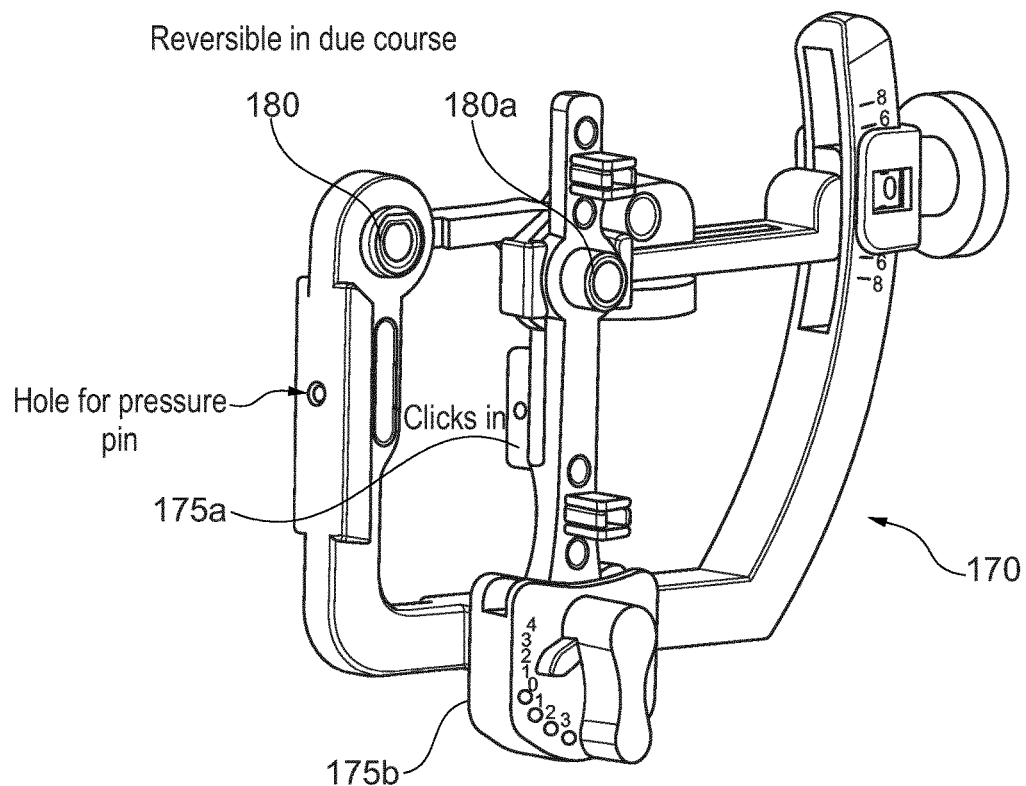
Figure 17D:
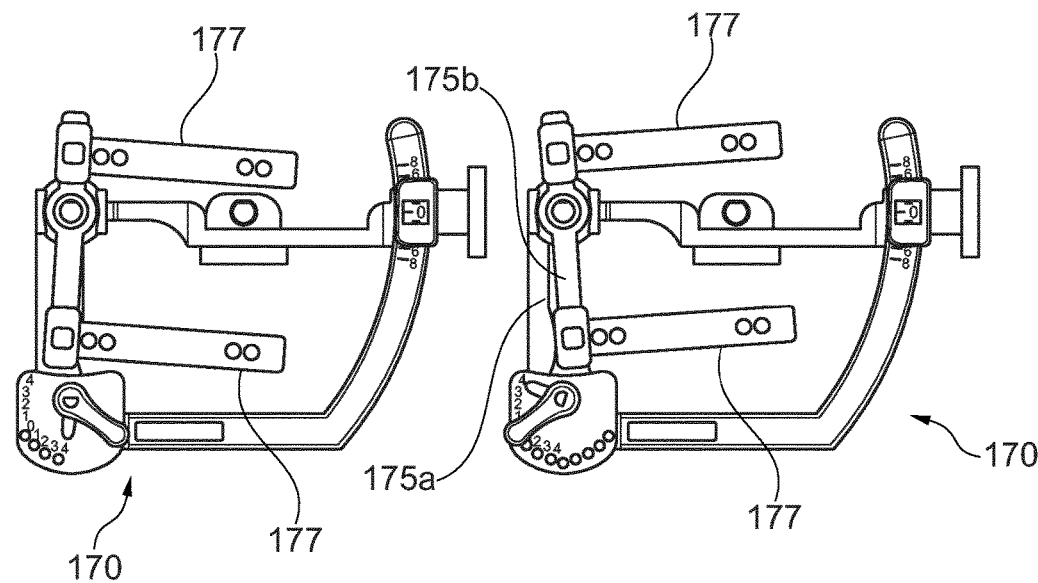
Figure 17E:
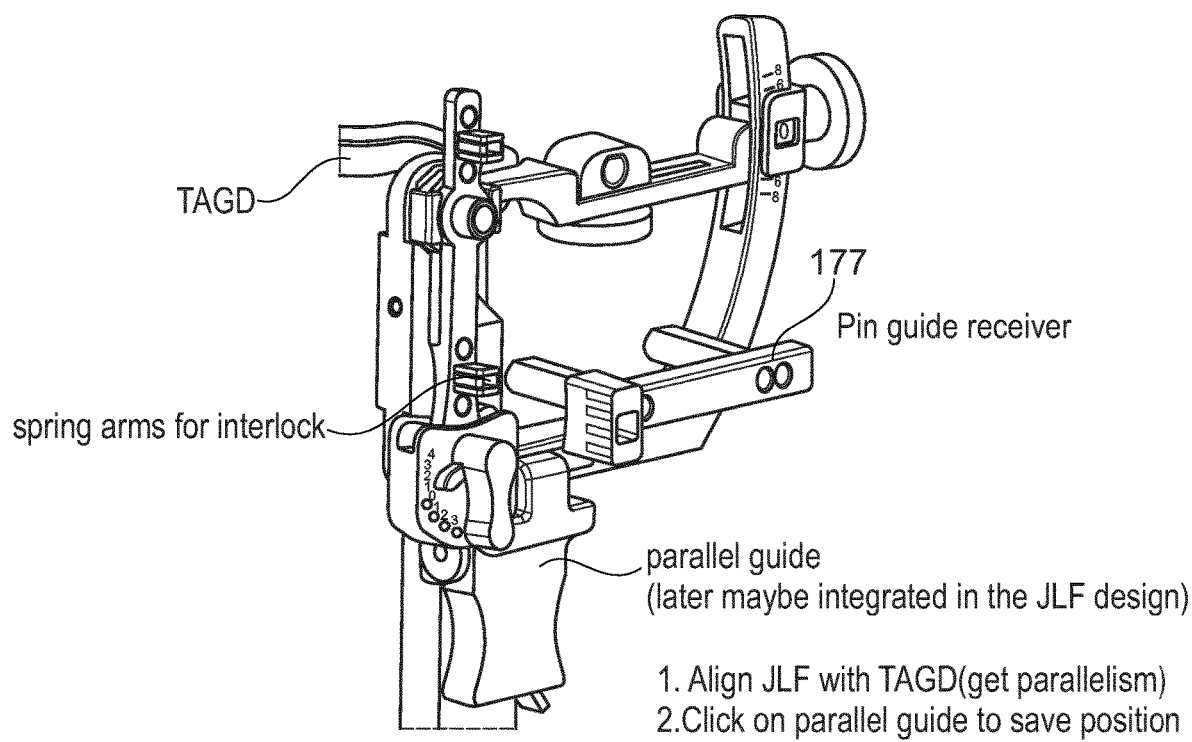

FIG. 17b shows the pin guide receivers for mounting to the pin guide receiver holes 174a and 174b on the pinning arm angular adjustment component 175. Different sizes of pin guide receivers 177 can be provided to account for different sizes of patients. For example a small pin guide receiver and a big pin guide receiver are shown in FIG. 17b. FIG. 17c shows the pinning arm angular adjustment component 175 separated from the joint level finder. The pinning arm angular adjustment component 175 clicks in to a hole on the first end of the mount of the joint level finder. A pressure pin holds the two devices together. FIG. 17d shows the joint level finder and pinning arm angular adjustment components attached together and shows pin guide receivers in place through the pin guide receiver holes. This figure shows how the pinning arm angular adjustment component can be adjusted so as to change the coronal slope of the pin guide receivers. FIG. 17e shows in greater detail the connection mechanism for attaching the pin guide receiver to the pinning arm angular adjustment component 175. Spring arms are provided between the pin guide receiver holes for interlock with the pin guide receivers or this could be by means of a screw or bayonet or another form of interlock. A parallel guide attaches the JLF to the the tibial extramedullary guide such that the mount of the JLF remains parallel to the axis of the tibial extramedullary guide. The parallel guide includes a projection which fits into a slot on the mount of the JLF such that the JLF can slide relative to the mount in the coronal plane. This allows the JLF to achieve the appropriate position for each patient.

Figure 17F:
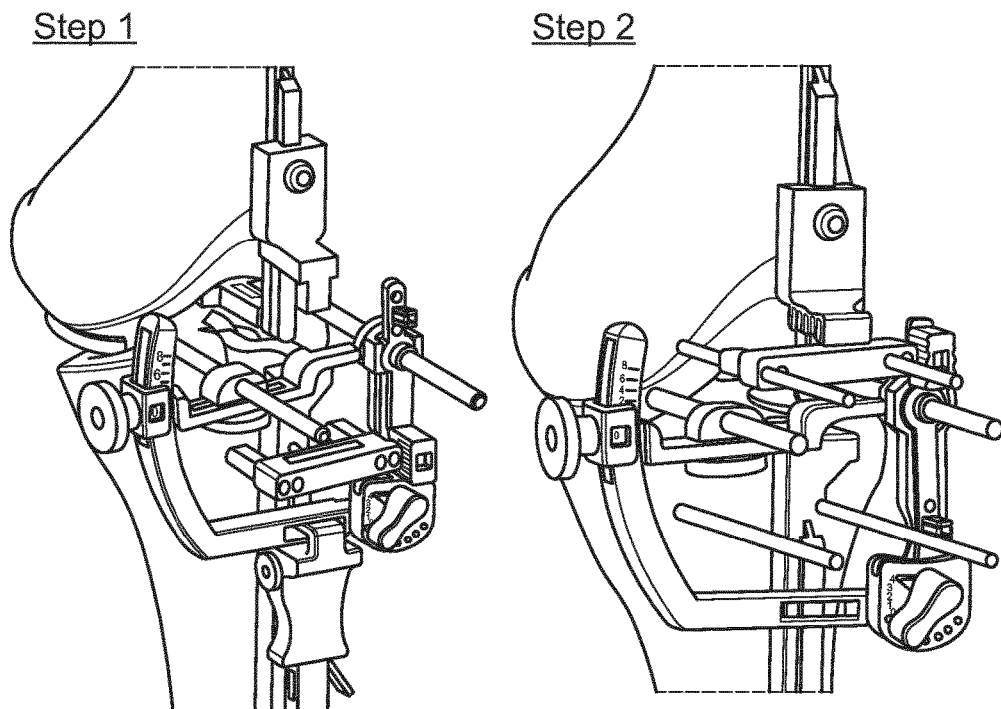

FIG. 17f shows the joint level finder mounted on the tibial alignment guide and distractor, with joint gap guides in position between the patient's tibia and femur. FIG. 17f shows a first step (step 1) of attaching the pin guide receiver 177 to the joint level finder and inserting pins into the tibia. Step 2 shows the pin guide receiver for the femur attached to the joint level finder and pins inserted into them, Bone resections can then be made relative to these pins.

The chassis carrying the JGGs can rotate relative to the main chassis (mount) of the JLF and there is a scale to display the rotational relationship in degrees. The main chassis has a projection across the distal section of the JLF with a slot that engages with the Tibial Alignment Guide and Distractor (TAGD) and aligns the main chassis of the JLF in parallel (in both coronal and sagittal planes) with the TAGD and hence the axis of the tibia. (The TAGD instrument has been previously described). The JLF (v.2) main chassis has a connection for the mounting of a further chassis (pining block carrying arm) with an angular adjustment coupling between the two.

In its function, the JLF (v.2) is introduced in to the knee articulation, the JGGs align the JGG chassis of the JLF (v.2) with the level of the joint in terms of both compartments. The main chassis is meanwhile coupled to the TAGD. The mobile articulation between the two chassis will permit the angle between the two chassis to be free to vary through the mobile articulation between the two. This articulation has a lock but would be unlocked at this stage. Once the relationship is established, the lock is engaged. The JLF (v.2) displays the angular relationship between the two chassis on the scale between the two.

The operator then attaches the pinning arm angular adjustment component to the main chassis. By default this is set to neutral, maintaining the pinning arms aligned with reference to the TAGD (and hence perpendicular to the axis of the tibia). The angular adjustment at the coupling between the main chassis and the pinning arms can be altered by the operator to change the relationship, guided by the displayed angle between the main chassis and the JGG chassis. The reason for providing a default position where the pinning arms are perpendicular to the axis of the tibia is to make the surgeon think about what they are doing. An adjustment to the angle must be concisely made, rather than blindly following the angle of the native joint level. Blindly following the native joint level indicated by the JLF may be problematic where the native joint level is greater than ±5 degrees, as explained before.

Then the pinning block is attached to the tibial pinning arm and pins placed in the tibia. Following this, the pinning block is lifted off, the TAGD to JLF (v.2) coupling detached, the pining block attached to the femoral pinning arm and the femoral IM rod coupled with the pinning block, orientating the JLF (v.2) with reference to the femoral IM rod (and hence the axis of the femur). However, this connection permits the orientation in the coronal plane of the JLF to be free to maintain the already established orientation relative to the TAGD already fixed whilst assuming the orientation in the sagittal plane with the femoral IM rod and hence the axis of the femur. The tibia is more accessible that the femur during the procedure, therefore the andle of the cut to the tibia is generally determined first, with the cut to the femur being referenced therefrom.

Pins are placed in the femur, the pinning block lifted off and the entire JLF can then be removed, leaving a pair of pins in the tibia and a pair in the distal femur. Subsequent resection of the tibial plateau and distal femur referenced from these pins would result in a rectangular (ie: balanced) extension gap of a specified size.

In a further aspect the JLF (v2) could be used in the flexed position of the knee to similarly pin for the resection of the flexion gap. In a yet further aspect the main and JGG chassis could be reversed so that the JLF (v.2) assumes a relationship to the JGGs by default but can be adjusted according to the angular relationship displayed between the JGG chassis and the TAGD. In a yet further aspect the joint distraction could be incorporated in the JLF rather than relying on the TAGD to distract the joint. (in flexion or extension). In a yet further aspect the distractor could be omitted and the JGGs alone relied upon to maintain the relative position of the femur and tibia with respect to the soft tissue envelope. In a yet further aspect the JLF could function with only one JGG to determine the joint height in only one compartment of the knee and align with reference to the tibial and/or femoral axis only.

FIGS. 18 to 24 show a flexion gap optimisation device 200 (instrument 9) which is used in determining the slope of the cut to the tibia in the sagittal plane. The pins placed in the tibia using the JLF provide a guide for a cut which would be perpendicular to the tibial axis in the sagittal plane. The FGOD adjusts the planned tibial resection sagittal slope to produce a flexion gap size that is close to the extension gap size and compatible with the selected femoral prosthesis size. The resultant sagittal slope of the tibia should be close to the patient's own native slope.

The point of contact between the articulating surfaces of the distal femur and the tibia in full extension is defined as one quarter of the distance from the anterior to posterior along the tibial plateau. The point of contact between the articulating surfaces of the distal femur and the tibia in flexion is defined as two thirds of the distance from the anterior to posterior along the tibial plateau. When the leg is in flexion the femur is rolled back onto its condyles which lie lower than the height of the distal end of the femur when the leg is in extension. As such, in order for the gap between the tibia and the femur to be equal in extension and flexion, the tibia must therefore be cut to be lower at the flexion point of contact than it is at the extension point of contact.

The FGOD includes a first chassis 202 including a first pair of holes 206 for sliding over pins placed in a tibia (those that are perpendicular to the tibial axis in the sagittal plane, as positioned by the JLF), and a second chassis 204 including second pair of holes 208 for guiding pins for insertion into said tibia. The first chassis 202 is connected to the second chassis 204 by a pivot joint 210, the second chassis 204 is pivotable about the pivot joint 210 so as to change the angle at which the second pair of holes 208 guides pins into the tibia relative to the angle of the pins through the first pair of holes 206. The chassis include slots 203, 205 with which the holes 206, 208 are aligned such that the apparatus and pins do not impinge on each other during movement of one chassis relative to the other. A scale 207 is provided on the first chassis of the FGOD 200, the scale displays the angle between first and second chassis and hence the angle between the first and second pairs of pin carriers.

When the first pair of holes 206 of the first chassis 202 is positioned over the pins placed in the tibia using the JLF (as described previously), the first chassis of the FGOD thus becomes orientated with the plane of the planned tibial resection determined earlier with the JLF, which in turn is based on the natural or native plane of the joint determined with the joint gap guides.

The first chassis 202 includes a side arm having a rail 226 for supporting a holder 220. The holder 220 has a first slot for receiving a bar 250 which attaches to a distal femoral surface block 230 (DFSB), as shown in FIG. 19, and a second slot for receiving a ruler support 222 which in turn receives a ruler 228 having a scale. The ruler support 222 has a projection 223 which extends into a slot 224 on the second chassis of the FGOD such that when the second chassis of the FGOD is moved relative to the first chassis, so as to change the projected posterior slope of the pins for insertion into the tibia, the ruler support 222 (and thus the ruler fixed within it) moves with it. The holder 220 attached to the first chassis 202 of the FGOD can slide along the rail 226 so as to adjust the position of the ruler (and the bar 250). The slot 224 on the second chassis extends parallel to the rail 226 so that when the holder 220 is moved along the rail 226 the projection 223 can slide along in the slot 224.

At the upper end of the bar 250 a blade 252 (not sharp) extends perpendicularly to the bar. The blade 252 slots into a slot in the distal femoral surface block. When held in the holder the blade is parallel with the main FGOD, and thus orientates the block to be parallel too. However, the block remains free to rotate around the blade (as the blade is smaller than the slot) and to translate from side to side within the limit of the fit of the blade inside the slot. The vertical bar 250 which connects the blade 252 to the main FGOD device can slide up and down in its slot in the holder 220, its vertical position being set by the surgeon dependent on the size of knee. A larger knee will require a distal femoral surface block that is further away from the tibia (and the FGOD main mechanism). Therefore the blade bar will be higher in its slot in the FGOD (and vice versa).

The distal femoral surface block includes a flat surface 234 for abutting the cut distal femur, a stylus 240 for abutting the anterior femur, and pairs of pin holes 232 for guiding pins into the distal femur to mark the position for the femoral cutting block (used later in the operation). The anterior femoral stylus bar 240 rests against the anterior femur and references the position of the anterior femur. It holds the distal femoral surface block level with the anterior femoral surface. The stylus has an adjustment for moving it back and forth (along the femur) with a scale marked for femoral prosthesis size. The distal femoral surface block is provided to make the anterior femoral resection to be level with the anterior femoral surface and the posterior femoral resection to be in the level required for the given size of femoral prosthesis being used. Femoral cutting blocks are provided corresponding to each size of femoral prosthesis.

FIG. 20 shows the anterior profile of the assembly of instrument 9 in which the FGOD is coupled with a ruler, blade, and the distal femoral surface block and stylus. The stylus bar is at the top and can rest on the anterior femur surface. The main chassis of the FGOD incorporates the two pairs of pin guides. The blade and scale connect the main chassis to the distal femur block by means of the blade engaging a slot on the block.

Figure 21:
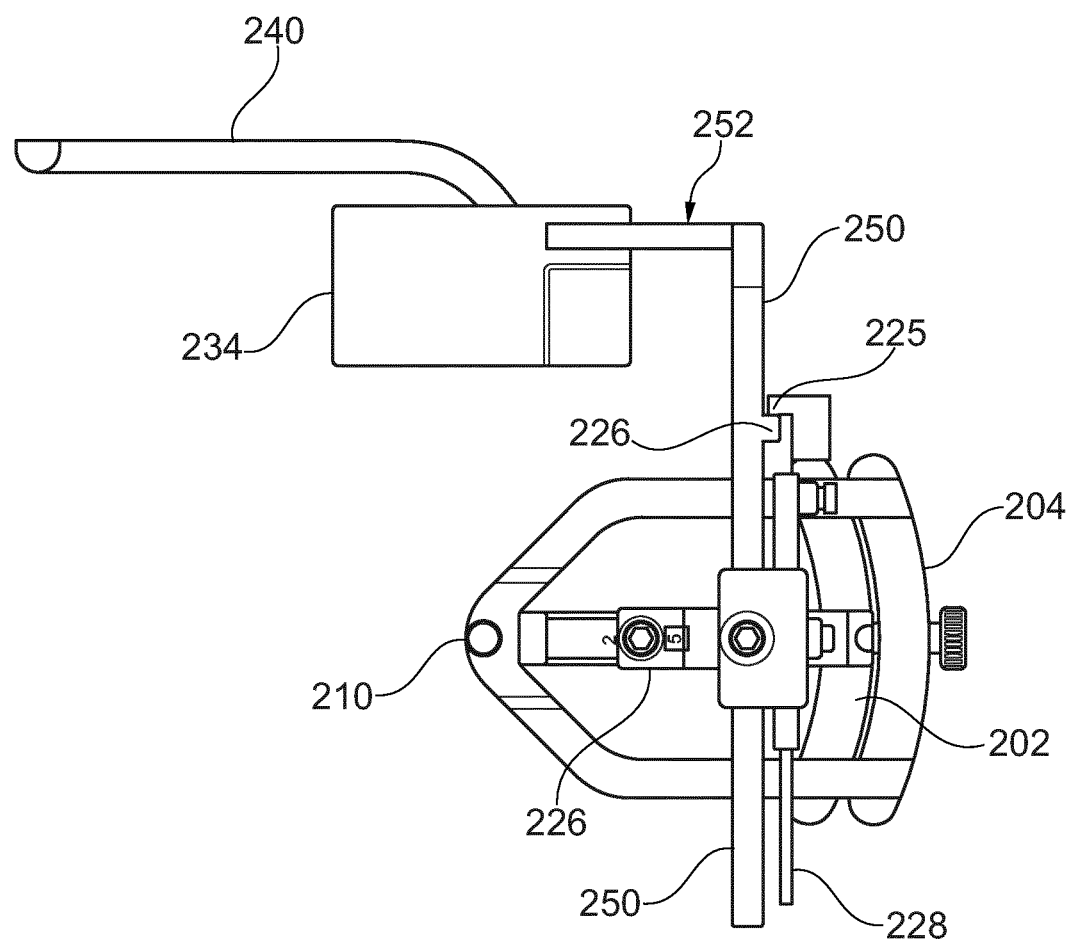

FIG. 21 shows a side profile of the assembly of instrument 9. The engagement of the blade within the slot can be seen. Depending on the variable distance between the femur and tibia, the blade may not engage the slot fully but its wide profile maintains the required relationship. The point of rotation of the two chassis of the FGOD is the apex of the chassis arms which is use is positioned against the surface of the tibia. The size scale for the blade stem carrier is seen on the chassis.

When looking at the FGOD attached to the patient's knee from the front of the knee, the ruler support 222 (and ruler in the support) is positioned immediately in front of the bar 250. The ruler includes a projection on its back 225 that abuts a projection 226 on the front of the blade bar. When the ruler is placed into the support 222 its projection 225 is moved down until it abuts the projection 226 on the bar 250 and the ruler is then locked into position in the ruler support 222. After they are locked together the ruler cannot move down any further relative to the bar. As the support is fixed to the second chassis, the ruler can however move upwards relative to the blade, with the support and the second chassis.

Before adjustment of the second chassis, the ruler indicates the height of the bar. There is a window in the slot in holder 220 through which the scale markings on the ruler can be seen. The ruler's scale indicates the sizes of femoral prostheses and therefore shows the size of the femoral implant suitable for the measured femur. The larger the knee and the higher the blade bar is resting, the higher the ruler will also be resting and the bigger the implant size will be shown. If the window shows that the patient's femur is between implant sizes the surgeon adjusts the position of the second chassis so that the number seen in the window is the next whole number. By moving the second chassis upward, the projected posterior slope is adjusted. The number of degrees of adjustment is shown on the scale on the front of the first chassis of the FGOD. The surgeon can check that this number of degrees is reasonable and adjust if required. The surgeon can use judgement as to whether it is best to go up a size of implant and set a steeper posterior slope on the tibia, or down a size with a shallower slope.

When the tibia is larger, a given angle of the second chassis relative to the first chassis will result in a greater gap between the tibia and femur at the flexion point of contact, compared to the same angle for a smaller tibia. To compensate for this, when the tibia of the patient is larger, the holder 22 is slid forward on the side rail of the FGOD, away from the patient. A given size of femur therefore requires a smaller angle between the first and second chassis for a larger tibia than it does for a smaller tibia. Trigonometry is employed to calculate the relative positioning of the parts to achieve the correct movement for the size of the implant.

During knee flexion, the femoral condyles roll back on the tibial plateau. This means that in extension the femur articulates with the higher anterior portion of the tibial plateau but in flexion the femur articulates with the lower posterior section of the tibial plateau. Anatomically the tibial plateau has a slope in the sagittal plane.

The FGOD adjusts the sagittal slope to comply with the individual patient anatomy whilst simultaneously producing a rectangular balanced flexion gap of the size matching the extension gap. In one embodiment the FGOD alters the sagittal slope of the tibial cut to match the anatomical for the patient but in a further embodiment it also does so with an adjustment made to accommodate the femoral component AP dimensions (which are incremental and finite).

The device is applied with the knee in flexion and distraction applied. The device includes two chassis that can rotate around each other about a point that corresponds to the location of the interface between femoral and tibial articulating surfaces in extension (¼ back from the most anterior part of the tibial plateau). In one embodiment the device is mounted onto the pins already placed in the tibia in extension. This orientates the device to lie parallel with the planned coronal slope of the tibial resection. In a further embodiment the device also consists of an accessory that is a femoral AP alignment block applied to the already resected distal surface of the femur and able to rotate and translate anteriorly and posteriorly. This block also incorporates an anterior femur referencing stylus bar. In one aspect the bar rests along the anterior surface of the distal femur and maintains the block in a position in which the anterior resection will be flush with the prominence of the anterior surface irrespective of the rotation.

In a further aspect the stylus bar incorporates an adjustment for translation proximally and distally with a scale indicating the size of femoral component being planned for determination of the appropriate level at which the stylus bar should be resting.

In a further embodiment the flexion gap optimisation device incorporates a blade that projects above it and engages a slot in the femoral distal surface block. This interlock holds the block parallel with instrument 9. In one aspect the blade can slide up and down relative to the instrument 9 chassis, assuming a position that places the stylus bar flush with the anterior femur (anterior referencing) with a scale marked on the blade stem indicating the femoral AP size measurement. In another aspect the blade stem holder on instrument 9 can slide up or down with a scale marked to correspond to the size of prostheses planned for measurement of femoral AP size in the relevant plane.

In a yet further embodiment the second chassis of instrument 9 can be adjusted by means of rotation relative to the first (static) chassis as previously described. In one aspect this movement also moves the point of read of the aforementioned scale, altering the size being measured.

In another aspect the movement directs two further pin guides to a position projecting at an angle to the extension joint level previously defined (referenced from the provisional pins placed earlier in extension) with an increased posterior sagittal slope, thereby increasing the size of the planned flexion gap, in accordance with the size of femoral component displayed on the scale and maintaining a constant desired flexion gap size. This is achieved because the interface between the articulating surfaces of the femur and tibia in 90 degrees of flexion is located more posteriorly (defined as ⅔ back from the anterior tibia). In yet another aspect the pin guides thus adjusted can place two new definitive pins for the tibial resection. The provisional pins may then be removed.

In a further embodiment the distal femoral block also contains pin guides for pins placed in the distal femur for the femoral AP resection block. In a further aspect this will be the size selected that corresponded to the tibial sagittal slope for which the tibial resection has been planned.

Prior art introduces an arbitrary slope to the sagittal slope of the tibial plateau bony resection, based on population averages and the prosthesis design but not related to that particular patients anatomy. To accommodate the given size of femoral component prior art either compromises the anterior position of the femoral component for a fixed flexion gap (posterior referencing) or it compromises the flexion gap for accurate anterior positioning (anterior referencing). The prior art determines the sagittal slope of the tibial cut independently of the femoral component AP dimension that is to be used. The femoral component AP sizes available for any non-custom made system are finite and incremental. Prior art employs styli with a point contact.

FIG. 22 shows another Flexion Gap Optimisation Device (FGOD v. 2). In this figure it can be seen that the stylus (anterior referencing bar) interlocks to the distal femoral surface block via a spring arm 242. The slope of the chassis relative to one another, and therefore the slope of the two pairs of pins guides is adjusted in a stepless manner by a threaded bolt arrangement.

FIGS. 23*a* to 23*g* show a pictorial guide to the use of the flexion gap optimisation device (instrument 9 "FGOD"). The femur is measured the anterior referencing bar is adjusted according to the size of the femur.

The knee is distracted and the femur and tibia are in their natural positions relative to each other, as directed by the tensioned soft tissue. The surgeon will first measure the lateral femoral condyle with a template to determine its size, and will compare the size with the prostheses to determine the closest prosthesis size available.

The FGOD is positioned over the tibial pins which were positioned in the tibia whilst the leg was in extension. The anterior referencing bar is adjusted according to femoral size and the DFSB and anterior referencing guide is then attached to the bar of the FGOD. The DFSB is pinned onto distal femur and the ruler is attached through the slot in the holder to measure the size of the patient's femur. The second chassis of the FGOD is adjusted so that the scale shows the next implant size up, then the final tibial pins can be inserted into the tibia.

When the FGOD assembly is positioned on the knee as described, the main FGOD will rest at the level of the tibial pins and the stylus rest against the anterior femur. The pins in the tibia are a certain constant distance below the centre of the joint as they were placed using the JLF and referenced from the joint gap guides. The size of the desired flexion gap is also constant (it is the thickness of the femoral and tibial prostheses combined). The scale on the ruler takes these into account. The projection on the blade bar will engage with the ruler and hold the ruler in the position that indicates the size of femoral component appropriate to the size of knee. This may be between sizes as the knee sizes are infinitely variable but the femoral component sizes manufactured will be incremental.

The slot for the ruler on the side of the main FGOD is connected to the moving part of the FGOD. Once positioned, the operator will engage a lock to secure the ruler to the moving part. The operator will then adjust the FGOD using the mechanism of the FGOD to angulate the moving part relative to the static chassis. This will also move the ruler and change the reading displayed on the ruler. The movement between the two parts of the FGOD may be through a pivot at the apex of the angulation (V.2). Alternatively the two parts may be connected together on a rail that follows an arc, the theoretical centre of the arc being the apex of the angulation but with no physical pivot (V.3).

As angulation of the moving part of the FGOD is introduced, the reading on the ruler indicating the femoral prosthesis size increases accordingly. The size displayed at any one time is the size of femoral prosthesis, which in conjunction with the degree of angulation of the planned tibial resection would produce the correct flexion gap size. Greater angulation of the tibial resection means a 'lower' tibial resection, hence a larger femoral prosthesis size becoming appropriate in order to maintain a constant flexion gap size.

The operator will adjust the FGOD until the desired combination of femoral prosthesis size and slope of tibial resection are being displayed on the FGOD scales, then place two new pins in the tibia through the pin carriers on the moving part of the FGOD. These will be used to align the subsequent tibial cutting block for the required resection. The first two pins will then be removed. The FGOD assembly is also removed, leaving behind pins in the tibia and femur for the definitive resections.

The FGOD incorporates an adjustment for the tibial size (anterior-posterior). The tibial size is measured using a simple ruler with a hook on the far end to engage the posterior margin of the tibial plateau. The adjustment (located on the side of the FGOD) moves the slots for the blade vertical bar and ruler anteriorly or posteriorly according to the markings in order to place the vertical plane at which the measurements are being made at the same distance from the apex of the angulation as the plane at which the flexion gap is defined. This means that for a larger tibia, the location of the flexion gap (ie: the point at which the surfaces of femur posterior condyle and tibia are in contact in flexion—this is two thirds of the distance in an anterior to posterior direction along the tibial plateau) is further away from the anterior surface of the tibia where the FGOD is located. Therefore, a lesser degree of angulation is required to produce the change in the vertical height of the tibial resection at the point at which the flexion gap is defined and vice versa. Locating the ruler in the appropriate position to represent the point at which the flexion gap would be measured takes this effect into account.

FIG. 24a shows another FGOD device (V.3), together with its associated components, from the anterior aspect whilst FIG. 24b shows the side view of the FGOD V.3. FGOD V.3 comprises a first chassis 212 and a second chassis 214, and other parts having reference numerals corresponding to those used in FIGS. 18-22.

The FGOD device (V.3) shown in FIG. 24 has the same function as the ones already described. Differences between v.3 and earlier versions include the theoretical, rather than physical, pivot point, and incorporation of a stylus bar with a dropping section in order to clear obstacles. The FGOD and FGOD V.2 use a pivot for the movement of the moveable chassis relative to the static chassis of the FGOD. The arc of movement which results in the desired angulation is based on the location of the pivot. The adjustment made by the FGOD is for the flexion gap without changing the extension gap. Thus the anterior part of the projected tibial resection should not change with the FGOD adjustment. The FGOD and FGOD V.2 place the pivot against the anterior surface of the tibia, such that the adjustment of the projected tibial resection starts from the anterior surface of the tibia. The V.3 FGOD mechanism for adjustment involves movement of one chassis against the other on a curved rail, and without a physical pivot. This means that the movement along the curved rail can follow an arc that has its centre of rotation theoretically located inside the tibia. Thus the pivot pint can be anywhere, including a theoretical point inside the tibia.

The FGOD shown in FIG. 24 uses a centre of rotation for the angular adjustment that is inside the tibia. The movement of the second chassis 214 relative to the first chassis 212 is produced by a curved rail with the aformentioned centre of rotation rather than being at a pivoting hinge outside the tibia. The point of contact between the articulating surfaces of the distal femur and tibia in full extension are defined as one quarter of the distance from anterior to posterior along the tibial plateau. In order for the adjustment to the sagittal slope of the tibial resection to determine the flexion gap size without also altering the extension gap size, the angulation of the tibial resection needs to occur around a pivot point at the point of contact for the extension gap. As this is inside the tibia, the FGOD V.3 employs a mechanism whereby the angulation between the two parts of the FGOD occurs by movement along a curved rail without a physical pivot. The curved rail has been calculated to have a centre of rotation located at the point of the extension gap.

FIG. 24c shows a schematic representation of the function of the flexion gap optimisation device (FGOD) 200. With the femur 300 and tibia 310 bones of the knee in 90 degrees flexion, the device is referencing the anterior femoral surface 301 and at the same time the pins 312 which were placed in the tibia in extension using the JLF device. According to these, the device measures the femoral anterior-posterior size, places pins in the distal femoral surface for the femoral posterior and anterior resections and also places additional pins in the tibia to guide the tibial resection so that it is at a sagittal angle that corresponds to the selected femoral size. Thus the FGOD interlinks the femoral and tibial resections to comply with each other from the onset.

FIG. 25 shows a schematic representation of the function of the JLF 100, whereby the centre of the joint gap is referenced using the joint gap guides 90 and pins 302, 304 are placed in the distal femur and tibia to act as references for the distal femoral and tibial resection levels. The pins are subsequently used to make resections for an extension gap of the prescribed size centred on the centre of the joint gap.

FIG. 26 shows how the pins 302, 304 placed using the JLF device are not affected by the presence of any fixed flexion deformity (FFD) of the knee joint. Arthritic knees often lose the ability to fully extend (straighten). This is called FFD. Following knee replacement surgery the factors preventing full extension are resolved and the knee can once again fully extend. Full extension is restored during surgery when abnormal bone growth (osteophytes) is removed and a contracted posterior capsule (the broad ligament at the back of the knee) is released. This can only be performed in the later stages of the operation when resections have been made and access to the back of the knee is obtained.

The resections in the distal femur and tibia need to be positioned so that the prosthesis will be in the correct position for full extension, once this has been achieved later in the operation. To satisfy this requirement, the JLF device (which determines the planes of resection for the tibia in extension and the distal femur) is employed in two stages. In the first it is aligned in parallel with tibial axis (by interlock with the tibial guide) and the pins placed in the tibia for the tibial resection position. The JLF is then disconnected from tibia and interlocked with the femoral guide, making it parallel with the femoral axis. Pins are then placed in the femur for the distal femoral resection. In the presence of FFD, the 'tilt' of the JLF as it moves from the tibial to the femoral position occurs on the joint gap guides which tilt in their positions in the joint space. As the centres of the joint gap guides remain in the same positions despite the tilt, the two resections are still centred on the centre of the joint and hence the resections are made for the knee as it would be in full extension. This method avoids any interference with the planning of the extension gap whether or not FFD may be present.

FIG. 27 shows a schematic representation of the centre of the joint gap 320 between the femur 300 and tibia 310 being identified in extension and the distal femoral resection 322 corresponding to this. Also shown is the height 324 of the anterior portion of the tibial resection corresponding to the extension gap. This process is achieved using the JLF device.

FIG. 28 shows a schematic representation of one of the principles employed by the invention. It shows the arc of motion of the knee from full extension to 90 degrees of flexion passing through the centre of the joint gaps identified in extension and in flexion and the tibial sagittal slope that accommodates this arc of motion.

FIG. 29 shows a schematic representation of the flexion gap being identified at the centre of the joint gap in flexion and the posterior femoral 326 and tibial 328 resections corresponding to this. The tibial resection anteriorly 330 is at the level identified in extension and posteriorly 332 at the level identified in flexion.

FIG. 30 shows a schematic representation of the function of one of the components of the FGOD 200. This is the distal femur surface block 230 which carries the bar shaped stylus 240 for referencing the anterior femoral surface, places pins in the distal femur for the femoral anterior and posterior resections and connects to the other FGOD components to measure the femoral anterior-posterior size. Also shown is the principle of measuring the femoral size and the influence on the flexion gap size of using the next larger or the next smaller femoral component.

FIG. 31 shows a schematic representation of the function of the FGOD 200 device main component. The device articulates to place additional pins (final tibial pins) 370 in the tibia with reference to the pins 380 placed earlier with the JLF device. The additional pins 370 are at a variable angle that corresponds to the tibial resection sagittal angle that would produce the correct flexion gap size for the given femoral component size.

In a further embodiment the surgical steps and technique described and the function of the instruments described can be adapted for a computer navigated technique. The joint gap guides and the joint level finder may be attached to a computer to determine the pre-diseased joint level so that the position of cuts can be determined.

A navigated system can use rigid bodies for optical or radiofrequency points of reference and registration steps as per standard. In one embodiment the joint distractor functions as per the manual technique in extension and flexion in turn. In a second embodiment the joint gaps are registered with a pointing device. In one aspect the opposing femoral and tibial articular surfaces are registered in flexion and extension. In a further aspect the software algorithm constructs from these points the centre of the gap (equivalent to the joint line) with an adjustment made by the surgeon when asymmetric wear is apparent. In a further aspect the algorithm extrapolates the curve through the centre of the gap in extension and flexion through which the joint movement is occuring. In a yet further aspect the extension and flexion rectangular gap balanced gaps can be planned on the planning screen. The planning takes place before any resections have been made or after only the distal femoral resection has been made so that the sagittal slope of the tibial resection can be incorporate into the planning for an optimised flexion gap as per the manual technique already described. The distal lateral femoral condyle surface is used as the point of reference for the joint line in order to optimise the patella-femoral joint tension in flexion, as already described.

In another embodiment the function of the flexion gap optimisation device is replicated by a software algorithm that varies the planned sagittal posterior slope of the tibial resection for an optimised flexion gap size for the given femoral component size.

FIG. 32 shows a distal femoral resection block assembly mounted on an intramedullary rod 430 in the femur 401 capable of making a resection of the distal femur measured from the surface of either the medial or the lateral femoral condyle at a variable angle and irrespective of which condyle is more prominent (the device is seen from above and from the side).

FIG. 32 shows the femur only femoral condyle referencing distal femoral resection device 400. This device is a variant of the JLF device. The device may function independently of the tibial guide and instead interlock to a conventional femoral intramedullary (IM) rod 430 with the knee in flexion. The device 400 includes a frame 440 having a slot 441 for receiving the stem 421 of a joint gap guide 420. The frame is mountable at a first end to a pinning block 410 for guiding pins to be placed in the distal femur and at a second end to a gauge block 550. The gauge block 450 is in turn mountable to a femoral intramedullary rod 430 and in use measures the relative orientation of the frame 440 relative to the intramedullary rod and therefore to the longitudinal axis of the femur. The gauge block can be used to fix the angle of the frame, and therefore of the line between the holes in the pinning block (and in turn the line of the cut to be made to the femur), relative to the longitudinal axis of the femur.

The frame includes a second slot 442 for receiving the stem of a second joint gap guide, however this is not essential. Where a second joint gap guide is used the knee may be held balanced in its pre-diseased position, but the cuts may still be planned referenced from the height of just one of the joint gap guides.

In this embodiment the device would be set by the operator in the coronal plane using an angular adjustment with reference to the IM rod. The joint gap guide 420 (or a simple stylus) is attached to the side facing the condyle from which the resection is to be measured (the lateral is preferred as explained hereinbefore). This could be the more prominent or the less prominent condyle. The pinning/cutting block 410 would then place pins in the femur for a distal femoral resection at a coronal angle measured by the gauge block 450 and referenced from the femoral IM rod 430. This instrument differs from prior art instruments because it uses a joint gap guide to determine the point from which the resection is measured. The joint gap guides are provided in a range of thicknesses as described hereinbefore. This means the degree of cartilage wear can be accounted for, rather than the prior art crude measure from the worn surface. In addition the invention can measure the resection size off the surface of either the medial or the lateral femoral condyle surface, irrespective of which is more prominent. Prior art instruments simply measure off a surface that comes to rest against the distal femur surface (inevitably the more prominent condyle surface). In this application the angle between the resection and the femoral rod is set by adjusting the connection between the two. In use the operator would select an angle that complies with the mechanical axis of the femur. Hence the plane of resection is at angle corresponding to a predetermined angle and the size of the resection is measured from the surface of the condyle against which the joint gap guide comes to rest. In this application conventional limb alignment and soft tissue releases may be needed but unlike the prior art equivalent instruments the joint level would be referenced from one or the other compartment as selected by the operator. A further advantage over prior art instruments is that the joint level can be made to correspond to that of the lateral compartment, avoiding a change in the position of the lateral femoral condyle when it is replaced by the prosthesis. This avoids increasing or decreasing the tension between the lateral femoral condyle and patella (which articulate against each other during knee motion) with resultant clinical benefit over prior art instruments. This limited functionality compared with the full JLF is a partial application of the surgical technique already described.

Embodiments of the invention described herein are directed at TKA surgery in particular, however, the concepts and instruments can also form part of an arthroplasty system for other joints in the body, or for a unicondylar knee replacement, for example.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosures in GB patent application numbers 1503242.8 and 1419876.6 from which this application claims priority, and in the abstract accompanying this application are incorporated herein by reference.

The invention claimed is:

1. An apparatus for finding the pre-diseased joint line of a knee, the knee comprising a femur having a lateral condyle and a medial condyle at its distal end, and a tibia having a longitudinal axis, the apparatus comprising:
a first gap guide for inserting between the tibia and the medial condyle of the femur and a second gap guide for inserting between the tibia and the lateral condyle of the femur, wherein the first and second gap guides each comprise a main body having a first surface for contacting the femur and a second surface for contacting the tibia, a centre-point lying half way between the first and second surfaces, and a handle extending from the main body; and
a frame comprising a first part having first and second holes for receiving the handles of the first and second gap guides respectively, wherein the original joint level of a patient's knee is taken as the line between the centre-point of the first gap guide and the centre-point of the second gap guide and the first part of the frame is adjustable such that the first and second holes can be moved closer to one another or further away from one another in a medial to lateral direction with respect to the joint.

2. The apparatus according to claim 1, wherein the first part of the frame supports the handles of the first and second gap guides such that they are parallel to one another.

3. The apparatus according to claim 1, wherein the apparatus includes a mount for attachment to an extramedullary rod for aligning with the axis of the tibia.

4. The apparatus according to claim 3, wherein the first part of the frame is pivotable relative to the mount.

5. The apparatus according to claim 3, wherein the apparatus includes a gauge for indicating the angle between the pre-diseased joint line and the mount.

6. The apparatus according to claim 3, wherein the first part of the frame is lockable relative to the mount.

7. The apparatus according to claim 1, wherein the frame includes a second part for supporting a pinning block.

8. The apparatus according to claim 7, wherein the apparatus includes gauge for indicating the angle of the second part of the frame relative to the pre-diseased joint line.

9. The apparatus according to claim 7, wherein the apparatus includes a mount, the second part of the frame pivotable relative to the mount, and a gauge for indicating the angle of the second part of the frame relative to the mount.

10. The apparatus according to claim 7, wherein the apparatus includes a pinning block supported by the second part of the frame.

11. The apparatus according to claim 1, wherein the apparatus includes a mount and the second part of the frame is pivotable relative to the mount.

12. A kit of parts, including at least two of:
(a) an apparatus for finding the pre-diseased joint line of a knee, the knee comprising a femur having a lateral condyle and a medial condyle at its distal end, and a tibia having a longitudinal axis, the apparatus comprising:
a first gap guide for inserting between the tibia and the medial condyle of the femur and a second gap guide for inserting between the tibia and the lateral condyle of the femur, wherein the gap guides each comprise a main body having a first surface for contacting the femur and a second surface for contacting the tibia, a centre-point lying half way between the first and second surfaces, and a handle extending from the main body; and a frame comprising a first part having first and second holes for receiving the handles of the first and second gap guides respectively, wherein the original joint level of a patient's knee is taken as the line between the centre-point of the first gap guide and the centre-point of the second gap guide and the first part of the frame is adjustable such that the first and second holes can be moved closer to one another or further away from one another in a medial to lateral direction with respect to the joint;

(b) an apparatus for determining the angle of a cut to be made to a tibia in the sagittal plane, the apparatus comprising:

a first chassis having a first pair of channels for receiving pins in a tibia; and a second chassis having a second pair of channels for receiving pins to be placed in a tibia;

wherein the second chassis is pivotable about a pivot point so as to change the angle of the second pair of channels relative to the first pair of channels; and (c) a distractor for separating the tibia and femur of a leg when the leg is extended, the distractor comprising:

first and second projections for inserting between the tibia and femur when the leg is extended, the first projection for contacting the tibial plateau and the second projection for inserting into a notch cut in the anterior distal femur; and a distraction mechanism for forcing the first and second projections away from one another so as to separate the tibia and femur in use.

* * * * *